US007260480B1

(12) United States Patent
Brown et al.

(10) Patent No.: US 7,260,480 B1
(45) Date of Patent: Aug. 21, 2007

(54) METHOD AND SYSTEM FOR INTEGRATING FEEDBACK LOOPS IN MEDICAL KNOWLEDGE DEVELOPMENT AND HEALTHCARE MANAGEMENT

(75) Inventors: Stephen J. Brown, Woodside, CA (US); Geoffrey J. Clapp, Mountain View, CA (US)

(73) Assignee: Health Hero Network, Inc., Redwood City, CA (US)

( * ) Notice: Subject to any disclaimer, the term of this patent is extended or adjusted under 35 U.S.C. 154(b) by 445 days.

(21) Appl. No.: 10/821,120

(22) Filed: Apr. 7, 2004

Related U.S. Application Data

(60) Provisional application No. 60/461,105, filed on Apr. 7, 2003, provisional application No. 60/461,526, filed on Apr. 8, 2003.

(51) Int. Cl.
| | | |
|---|---|---|
| *G06F 19/00* | (2006.01) | |
| *G06F 15/00* | (2006.01) | |
| *G06F 17/30* | (2006.01) | |
| *G06G 7/60* | (2006.01) | |

(52) U.S. Cl. ............................. 702/19; 700/1; 703/11; 707/3

(58) Field of Classification Search ..................... None
See application file for complete search history.

(56) References Cited

U.S. PATENT DOCUMENTS

| | | | |
|---|---|---|---|
| 3,426,150 A | 2/1969 | Tygart | |
| 3,566,365 A | 2/1971 | Rawson et al. | |
| 3,566,370 A | 2/1971 | Worthington, Jr. et al. | |
| 3,581,072 A | 5/1971 | Nymeyer | |
| 3,768,014 A | 10/1973 | Smith | |
| 3,811,116 A | 5/1974 | Takeuchi et al. | |
| 3,883,235 A | 5/1975 | Lynn et al. | |
| 3,910,257 A | 10/1975 | Fletcher et al. | |
| 3,920,005 A | 11/1975 | Gombrich et al. | |
| 3,996,928 A | 12/1976 | Marx | |
| 4,004,577 A | 1/1977 | Sarnoff | |
| 4,051,522 A | 9/1977 | Healy et al. | |
| 4,060,915 A | 12/1977 | Conway | |
| 4,130,881 A | 12/1978 | Haessler et al. | |
| 4,150,284 A | 4/1979 | Trenkler et al. | |
| 4,151,407 A | 4/1979 | McBride et al. | |
| 4,151,831 A | 5/1979 | Lester | |
| 4,173,971 A | 11/1979 | Karz | |
| 4,216,462 A | 8/1980 | McGrath et al. | |
| 4,227,526 A | 10/1980 | Goss | |
| 4,253,521 A | 3/1981 | Savage | |
| 4,259,548 A | 3/1981 | Fahey et al. | |
| 4,270,547 A | 6/1981 | Steffen et al. | |
| 4,296,756 A | 10/1981 | Dunning et al. | |
| 4,347,568 A | 8/1982 | Giguere et al. | |
| 4,347,851 A | 9/1982 | Jundanian | |
| 4,360,345 A | 11/1982 | Hon | |
| 4,412,287 A | 10/1983 | Braddock, III | |
| 4,417,306 A | 11/1983 | Citron et al. | |
| 4,422,081 A | 12/1983 | Woods et al. | |
| 4,428,733 A | 1/1984 | Kumar-Misir | |
| 4,449,536 A | 5/1984 | Weaver | |
| 4,465,077 A * | 8/1984 | Schneider .................... 600/551 |
| 4,473,884 A | 9/1984 | Behl | |
| 4,518,361 A | 5/1985 | Conway | |
| 4,519,398 A | 5/1985 | Lisiecki et al. | |
| 4,531,527 A | 7/1985 | Reinhold, Jr. | |
| 4,546,436 A | 10/1985 | Schneider et al. | |
| 4,566,461 A | 1/1986 | Lubell et al. | |
| 4,576,578 A | 3/1986 | Parker et al. | |
| 4,592,546 A | 6/1986 | Fascenda et al. | |
| 4,627,445 A | 12/1986 | Garcia | |
| 4,674,652 A | 6/1987 | Aten et al. | |
| 4,686,624 A | 8/1987 | Blum et al. | |
| 4,694,490 A | 9/1987 | Harvey et al. | |
| 4,695,954 A | 9/1987 | Rose et al. | |
| 4,712,562 A | 12/1987 | Ohayon et al. | |
| 4,722,349 A | 2/1988 | Baumberg | |
| 4,729,381 A | 3/1988 | Harada et al. | |
| 4,730,253 A | 3/1988 | Gordon | |
| 4,731,726 A | 3/1988 | Allen, III | |
| 4,738,451 A | 4/1988 | Logg | |
| 4,768,229 A | 8/1988 | Benjamin et al. | |
| 4,779,199 A | 10/1988 | Yoneda et al. | |
| 4,782,511 A | 11/1988 | Nemec et al. | |
| 4,789,928 A | 12/1988 | Fujisaki | |
| 4,796,639 A | 1/1989 | Snow et al. | |
| 4,799,156 A | 1/1989 | Shavit et al. | |
| 4,799,199 A | 1/1989 | Scales, III et al. | |
| 4,803,625 A | 2/1989 | Fu et al. | |
| 4,835,372 A | 5/1989 | Gombrich et al. | |
| 4,838,275 A | 6/1989 | Lee | |

(Continued)

FOREIGN PATENT DOCUMENTS

EP          0251520          7/1988

(Continued)

OTHER PUBLICATIONS

"Blood Glucose Monitors", *Portable Health Device*, (1988), vol. 17(9), pp. 253-271.

(Continued)

*Primary Examiner*—John S Brusca
(74) *Attorney, Agent, or Firm*—Christopher P. Maiorana, PC

(57) ABSTRACT

A system and method are described for processing medical knowledge. The system comprises a database, a rendering engine and a feedback engine. The database may include medical knowledge sources, wherein an ontology specifies how the medical knowledge sources apply to specific disease conditions and patient populations. The rendering engine may convert medical knowledge obtained from the medical knowledge sources to a format suitable for a presentation to a patient on a selected patient device. The feedback engine may receive feedback from a plurality of patients and to provide feedback data to the database and the knowledge sources.

19 Claims, 25 Drawing Sheets

U.S. PATENT DOCUMENTS

| | | |
|---|---|---|
| 4,846,797 A | 7/1989 | Howson et al. |
| 4,853,521 A | 8/1989 | Claeys et al. |
| 4,858,354 A | 8/1989 | Gettler |
| 4,858,617 A | 8/1989 | Sanders |
| 4,890,621 A | 1/1990 | Hakky |
| 4,894,777 A | 1/1990 | Negishi et al. |
| 4,897,869 A | 1/1990 | Takahashi |
| 4,899,839 A | 2/1990 | Dessertine et al. |
| 4,903,201 A | 2/1990 | Wagner |
| 4,907,973 A | 3/1990 | Hon |
| 4,916,441 A | 4/1990 | Gombrich |
| 4,931,934 A | 6/1990 | Snyder |
| 4,933,873 A | 6/1990 | Kaufman et al. |
| 4,933,876 A | 6/1990 | Markoff et al. |
| 4,950,246 A | 8/1990 | Muller |
| 4,950,264 A | 8/1990 | Osborn, III |
| 4,953,552 A | 9/1990 | DeMarzo |
| 4,958,632 A | 9/1990 | Duggan |
| 4,958,641 A | 9/1990 | Digby et al. |
| 4,967,756 A | 11/1990 | Hewitt |
| 4,977,899 A | 12/1990 | Digby et al. |
| 4,978,303 A | 12/1990 | Lampbell |
| 4,978,335 A | 12/1990 | Arthur, III |
| 4,979,509 A | 12/1990 | Hakky |
| 5,007,429 A | 4/1991 | Treatch et al. |
| 5,009,645 A | 4/1991 | Silver et al. |
| 5,016,172 A | 5/1991 | Dessertine |
| 5,019,974 A | 5/1991 | Beckers |
| 5,024,225 A | 6/1991 | Fang |
| 5,025,374 A | 6/1991 | Roizen et al. |
| 5,034,807 A | 7/1991 | Von Kohorn |
| 5,035,625 A | 7/1991 | Munson et al. |
| 5,036,462 A | 7/1991 | Kaufman et al. |
| 5,049,487 A | 9/1991 | Phillips et al. |
| 5,050,612 A | 9/1991 | Matsumura |
| 5,056,059 A | 10/1991 | Tivig et al. |
| 5,059,394 A | 10/1991 | Phillips et al. |
| 5,065,315 A | 11/1991 | Garcia et al. |
| 5,068,536 A | 11/1991 | Rosenthal |
| 5,074,317 A | 12/1991 | Bondell et al. |
| 5,077,476 A | 12/1991 | Rosenthal |
| 5,077,665 A | 12/1991 | Silverman et al. |
| 5,095,798 A | 3/1992 | Okada et al. |
| 5,104,380 A | 4/1992 | Holman et al. |
| 5,109,414 A | 4/1992 | Harvey et al. |
| 5,109,974 A | 5/1992 | Beer et al. |
| 5,111,396 A | 5/1992 | Mills et al. |
| 5,111,817 A | 5/1992 | Clark et al. |
| 5,111,818 A | 5/1992 | Suzuki et al. |
| 5,120,230 A | 6/1992 | Clark et al. |
| 5,120,421 A | 6/1992 | Glass et al. |
| 5,128,552 A | 7/1992 | Fang et al. |
| 5,128,752 A | 7/1992 | Von Kohorn |
| 5,134,391 A | 7/1992 | Okada |
| 5,142,358 A | 8/1992 | Jason |
| 5,142,484 A | 8/1992 | Kaufman et al. |
| 5,143,378 A | 9/1992 | Joel |
| 5,171,977 A | 12/1992 | Morrison |
| 5,176,502 A | 1/1993 | Sanderson et al. |
| 5,182,707 A | 1/1993 | Cooper et al. |
| 5,204,670 A | 4/1993 | Stinton |
| 5,219,322 A | 6/1993 | Weathers |
| 5,222,020 A | 6/1993 | Takeda |
| 5,226,895 A | 7/1993 | Harris |
| 5,227,874 A | 7/1993 | Von Kohorn |
| 5,228,450 A | 7/1993 | Sellers |
| 5,230,629 A | 7/1993 | Buschke |
| 5,231,990 A | 8/1993 | Gauglitz |
| 5,243,515 A | 9/1993 | Lee |
| 5,249,044 A | 9/1993 | Von Kohorn |
| 5,251,126 A | 10/1993 | Kahn et al. |
| 5,261,401 A | 11/1993 | Baker et al. |
| 5,262,943 A | 11/1993 | Thibado et al. |
| 5,265,888 A | 11/1993 | Yamamoto et al. |
| 5,266,179 A | 11/1993 | Nankai et al. |
| 5,275,159 A | 1/1994 | Griebel |
| 5,282,950 A | 2/1994 | Dietze |
| 5,295,491 A | 3/1994 | Gevins |
| 5,299,121 A | 3/1994 | Brill et al. |
| 5,301,105 A | 4/1994 | Cummings, Jr. |
| 5,304,112 A | 4/1994 | Mrklas et al. |
| 5,304,468 A | 4/1994 | Phillips |
| 5,307,263 A | 4/1994 | Brown |
| 5,309,919 A | 5/1994 | Snell et al. |
| 5,321,009 A | 6/1994 | Baeder et al. |
| 5,325,288 A | 6/1994 | Satou |
| 5,329,459 A | 7/1994 | Kaufman et al. |
| 5,329,608 A | 7/1994 | Bocchiere et al. |
| 5,331,549 A | 7/1994 | Crawford, Jr. |
| 5,333,981 A | 8/1994 | Pronovost et al. |
| 5,335,338 A | 8/1994 | Proesel |
| 5,339,821 A | 8/1994 | Fujimoto |
| 5,341,291 A | 8/1994 | Roizen et al. |
| 5,343,239 A | 8/1994 | Lappington et al. |
| 5,344,324 A | 9/1994 | O'Donnell et al. |
| 5,357,427 A | 10/1994 | Langen et al. |
| 5,366,896 A | 11/1994 | Margrey et al. |
| 5,368,562 A | 11/1994 | Blomquist et al. |
| 5,371,687 A | 12/1994 | Holmes, II et al. |
| 5,375,604 A | 12/1994 | Kelly et al. |
| 5,377,100 A | 12/1994 | Pope et al. |
| 5,390,238 A | 2/1995 | Kirk et al. |
| 5,399,821 A | 3/1995 | Inagaki et al. |
| 5,410,471 A | 4/1995 | Alyfuku et al. |
| 5,410,474 A | 4/1995 | Fox |
| 5,429,140 A | 7/1995 | Burdea et al. |
| 5,431,690 A | 7/1995 | Schaldach et al. |
| 5,431,691 A | 7/1995 | Snell et al. |
| 5,434,611 A | 7/1995 | Tamura |
| 5,438,607 A | 8/1995 | Przygoda, Jr. et al. |
| 5,438,983 A | 8/1995 | Falcon |
| 5,441,047 A | 8/1995 | David et al. |
| 5,449,334 A | 9/1995 | Kingsbury |
| 5,454,721 A | 10/1995 | Kuch |
| 5,454,722 A | 10/1995 | Holland et al. |
| 5,456,606 A | 10/1995 | McIntyre |
| 5,456,692 A | 10/1995 | Smith, Jr. et al. |
| 5,458,123 A | 10/1995 | Unger |
| 5,467,269 A | 11/1995 | Flaten |
| 5,471,039 A | 11/1995 | Irwing, Jr. et al. |
| 5,471,382 A | 11/1995 | Tallman et al. |
| 5,483,276 A | 1/1996 | Brooks et al. |
| 5,488,412 A | 1/1996 | Majeti et al. |
| 5,488,423 A | 1/1996 | Walkingshaw et al. |
| 5,501,231 A | 3/1996 | Kaish |
| 5,502,636 A | 3/1996 | Clarke |
| 5,502,726 A | 3/1996 | Fischer |
| 5,504,519 A | 4/1996 | Remillard |
| 5,517,405 A | 5/1996 | McAndrew et al. |
| 5,518,001 A | 5/1996 | Snell |
| 5,519,058 A | 5/1996 | Gonick et al. |
| 5,519,433 A | 5/1996 | Lappington et al. |
| 5,523,232 A | 6/1996 | Sechler |
| 5,536,249 A | 7/1996 | Castellano et al. |
| 5,542,420 A | 8/1996 | Goldman et al. |
| 5,544,649 A | 8/1996 | David et al. |
| 5,546,943 A | 8/1996 | Gould |
| 5,549,117 A | 8/1996 | Tacklind et al. |
| 5,550,575 A | 8/1996 | West et al. |
| 5,553,609 A | 9/1996 | Chen |
| 5,558,638 A | 9/1996 | Evers et al. |
| 5,564,429 A | 10/1996 | Bornn et al. |
| 5,569,212 A | 10/1996 | Brown |
| 5,572,421 A | 11/1996 | Altman et al. |

| Patent No. | Date | Inventor |
|---|---|---|
| 5,572,646 A | 11/1996 | Kawai et al. |
| 5,574,828 A | 11/1996 | Hayward et al. |
| 5,576,952 A | 11/1996 | Stutman et al. |
| 5,583,758 A | 12/1996 | McIlroy et al. |
| 5,590,648 A | 1/1997 | Mitchell et al. |
| 5,593,349 A | 1/1997 | Miguel et al. |
| 5,593,390 A | 1/1997 | Castellano et al. |
| 5,594,637 A | 1/1997 | Eisenberg et al. |
| 5,596,994 A | 1/1997 | Bro |
| 5,597,307 A | 1/1997 | Redford et al. |
| 5,601,435 A | 2/1997 | Quy |
| 5,613,495 A | 3/1997 | Mills et al. |
| 5,619,991 A | 4/1997 | Sloane |
| 5,624,265 A | 4/1997 | Redford et al. |
| 5,628,309 A | 5/1997 | Brown |
| 5,629,981 A | 5/1997 | Nerlikar |
| 5,631,844 A | 5/1997 | Margrey et al. |
| 5,633,910 A | 5/1997 | Cohen |
| 5,635,532 A | 6/1997 | Samid |
| 5,640,569 A | 6/1997 | Miller et al. |
| 5,640,953 A | 6/1997 | Bishop et al. |
| 5,642,731 A | 7/1997 | Kehr |
| 5,642,936 A | 7/1997 | Evans |
| 5,651,363 A | 7/1997 | Kaufman et al. |
| 5,651,775 A | 7/1997 | Walker et al. |
| 5,659,691 A | 8/1997 | Durward et al. |
| 5,666,487 A | 9/1997 | Goodman et al. |
| 5,670,711 A | 9/1997 | Detournay et al. |
| 5,675,635 A | 10/1997 | Vos et al. |
| 5,678,562 A | 10/1997 | Sellers |
| 5,678,571 A | 10/1997 | Brown |
| 5,679,075 A | 10/1997 | Forrest et al. |
| 5,680,590 A | 10/1997 | Parti |
| 5,680,866 A | 10/1997 | Kangas et al. |
| 5,687,322 A | 11/1997 | Deaton et al. |
| 5,687,717 A | 11/1997 | Halpern et al. |
| 5,687,734 A | 11/1997 | Dempsey et al. |
| 5,689,652 A | 11/1997 | Lupien et al. |
| 5,692,906 A | 12/1997 | Corder |
| 5,704,364 A | 1/1998 | Saltzstein et al. |
| 5,704,366 A | 1/1998 | Tacklind et al. |
| 5,704,902 A | 1/1998 | Vandenbelt et al. |
| 5,704,922 A | 1/1998 | Brown |
| 5,710,178 A | 1/1998 | Samid |
| 5,710,918 A | 1/1998 | Lagarde et al. |
| 5,711,297 A | 1/1998 | Iliff |
| 5,714,319 A | 2/1998 | Joutel et al. |
| 5,715,451 A | 2/1998 | Marlin |
| 5,715,823 A | 2/1998 | Wood et al. |
| 5,717,739 A | 2/1998 | Dyer et al. |
| 5,717,913 A | 2/1998 | Driscoll |
| 5,720,733 A | 2/1998 | Brown |
| 5,722,418 A | 3/1998 | Bro |
| 5,727,153 A | 3/1998 | Powell |
| 5,730,124 A | 3/1998 | Yamauchi |
| 5,730,654 A | 3/1998 | Brown |
| 5,732,696 A | 3/1998 | Rapoport et al. |
| 5,732,709 A | 3/1998 | Tacklind et al. |
| 5,734,413 A | 3/1998 | Lappington et al. |
| 5,749,083 A | 5/1998 | Koda et al. |
| 5,752,234 A | 5/1998 | Withers |
| 5,754,740 A | 5/1998 | Fukuoka et al. |
| 5,760,771 A | 6/1998 | Blonder et al. |
| 5,772,585 A | 6/1998 | Lavin et al. |
| 5,778,882 A | 7/1998 | Raymond et al. |
| 5,782,814 A | 7/1998 | Brown et al. |
| 5,785,650 A | 7/1998 | Akasaka et al. |
| 5,787,295 A | 7/1998 | Nakao |
| 5,791,342 A | 8/1998 | Woodard |
| 5,792,117 A | 8/1998 | Brown |
| 5,793,969 A | 8/1998 | Kamentsky et al. |
| 5,794,219 A | 8/1998 | Brown |
| 5,794,251 A | 8/1998 | Watanabe et al. |
| 5,796,393 A | 8/1998 | MacNaughton |
| 5,799,318 A | 8/1998 | Cardinal et al. |
| 5,800,458 A | 9/1998 | Wingrove |
| 5,802,494 A | 9/1998 | Kuno |
| 5,802,534 A | 9/1998 | Hatayama et al. |
| 5,806,057 A | 9/1998 | Gormley et al. |
| 5,810,747 A | 9/1998 | Brudny et al. |
| 5,819,735 A | 10/1998 | Mansfield et al. |
| 5,822,544 A | 10/1998 | Chaco et al. |
| 5,822,715 A | 10/1998 | Worthington et al. |
| 5,825,283 A | 10/1998 | Camhi |
| 5,827,180 A | 10/1998 | Goodman |
| 5,828,943 A | 10/1998 | Brown |
| 5,832,448 A | 11/1998 | Brown |
| 5,835,896 A | 11/1998 | Fisher et al. |
| 5,840,020 A | 11/1998 | Heinonen et al. |
| 5,842,976 A | 12/1998 | Williamson |
| 5,868,669 A | 2/1999 | Iliff |
| 5,868,683 A | 2/1999 | Protopapas et al. |
| 5,875,432 A | 2/1999 | Sehr |
| 5,879,163 A | 3/1999 | Brown et al. |
| 5,882,338 A | 3/1999 | Gray |
| 5,887,133 A | 3/1999 | Brown et al. |
| 5,893,077 A | 4/1999 | Griffin |
| 5,893,098 A | 4/1999 | Peters et al. |
| 5,897,493 A | 4/1999 | Brown |
| 5,899,855 A | 5/1999 | Brown |
| 5,911,687 A | 6/1999 | Sato et al. |
| 5,913,310 A | 6/1999 | Brown |
| 5,918,603 A | 7/1999 | Brown |
| 5,920,477 A | 7/1999 | Hofbert et al. |
| 5,933,136 A | 8/1999 | Brown |
| 5,935,060 A | 8/1999 | Iliff |
| 5,940,801 A | 8/1999 | Brown |
| 5,941,829 A | 8/1999 | Saltzstein et al. |
| 5,945,651 A | 8/1999 | Chorosinski et al. |
| 5,951,300 A | 9/1999 | Brown |
| 5,954,641 A | 9/1999 | Kehr et al. |
| 5,956,501 A | 9/1999 | Brown |
| 5,960,403 A | 9/1999 | Brown |
| 5,961,446 A | 10/1999 | Beller et al. |
| 5,966,526 A | 10/1999 | Yokoi |
| 5,971,855 A | 10/1999 | Ng |
| 5,971,922 A | 10/1999 | Arita et al. |
| 5,983,003 A | 11/1999 | Lection et al. |
| 5,983,217 A | 11/1999 | Khosravi-Sichani et al. |
| 5,987,471 A | 11/1999 | Bodine et al. |
| 5,995,969 A | 11/1999 | Lee et al. |
| 5,997,476 A | 12/1999 | Brown |
| 5,997,502 A | 12/1999 | Reilly et al. |
| 6,001,065 A | 12/1999 | DeVito |
| 6,022,315 A | 2/2000 | Iliff |
| 6,022,615 A | 2/2000 | Rettenbacher |
| 6,023,686 A | 2/2000 | Brown |
| 6,024,281 A | 2/2000 | Shepley |
| 6,029,138 A | 2/2000 | Khorasani et al. |
| 6,032,119 A | 2/2000 | Brown et al. |
| 6,035,328 A | 3/2000 | Soukal |
| 6,046,761 A | 4/2000 | Echerer |
| 6,049,794 A | 4/2000 | Jacobs et al. |
| 6,050,940 A | 4/2000 | Braun et al. |
| 6,055,314 A | 4/2000 | Spies et al. |
| 6,055,487 A | 4/2000 | Margery et al. |
| 6,055,506 A | 4/2000 | Frasca, Jr. |
| 6,057,758 A | 5/2000 | Dempsey et al. |
| 6,068,615 A | 5/2000 | Brown et al. |
| 6,095,985 A | 8/2000 | Raymond et al. |
| 6,101,478 A | 8/2000 | Brown |
| 6,110,148 A | 8/2000 | Brown et al. |
| 6,113,578 A | 9/2000 | Brown |
| 6,138,145 A | 10/2000 | Kawanaka |
| 6,144,837 A | 11/2000 | Quy |
| 6,151,586 A | 11/2000 | Brown |

| | | |
|---|---|---|
| 6,161,095 A | 12/2000 | Brown |
| 6,167,362 A | 12/2000 | Brown et al. |
| 6,167,386 A | 12/2000 | Brown |
| 6,168,563 B1 | 1/2001 | Brown |
| 6,177,940 B1 | 1/2001 | Bond et al. |
| 6,186,145 B1 | 2/2001 | Brown |
| 6,188,988 B1 * | 2/2001 | Barry et al. ................... 705/3 |
| 6,189,029 B1 | 2/2001 | Fuerst |
| D439,242 S | 3/2001 | Brown et al. |
| 6,196,970 B1 * | 3/2001 | Brown ....................... 600/300 |
| 6,210,272 B1 | 4/2001 | Brown |
| 6,221,012 B1 | 4/2001 | Maschke et al. |
| 6,233,539 B1 | 5/2001 | Brown |
| 6,240,393 B1 | 5/2001 | Brown |
| 6,248,065 B1 | 6/2001 | Brown |
| 6,260,022 B1 | 7/2001 | Brown |
| 6,270,455 B1 | 8/2001 | Brown |
| 6,270,456 B1 | 8/2001 | Iliff |
| 6,334,778 B1 | 1/2002 | Brown |
| 6,352,523 B1 | 3/2002 | Brown et al. |
| 6,368,273 B1 | 4/2002 | Brown |
| 6,370,513 B1 | 4/2002 | Kolawa et al. |
| 6,375,469 B1 | 4/2002 | Brown |
| 6,379,301 B1 | 4/2002 | Worthington et al. |
| 6,381,577 B1 | 4/2002 | Brown |
| 6,436,036 B1 | 8/2002 | Miller-Kovach et al. |
| 6,513,532 B2 | 2/2003 | Mault et al. |
| 2002/0019748 A1 | 2/2002 | Brown |
| 2004/0106855 A1 | 6/2004 | Brown |
| 2004/0107116 A1 | 6/2004 | Brown |
| 2004/0117207 A1 | 6/2004 | Brown |
| 2004/0117208 A1 | 6/2004 | Brown |
| 2004/0117209 A1 | 6/2004 | Brown |
| 2004/0117210 A1 | 6/2004 | Brown |

FOREIGN PATENT DOCUMENTS

| | | |
|---|---|---|
| EP | 0286456 | 10/1988 |
| EP | 0320749 | 2/1989 |
| EP | 370599 | 5/1990 |
| EP | 0461910 | 12/1991 |
| EP | 508912 | 10/1992 |
| EP | 526166 | 2/1993 |
| EP | 0558975 | 9/1993 |
| EP | 0653718 | 11/1994 |
| EP | 676709 | 10/1995 |
| EP | 680727 | 11/1995 |
| EP | 761160 | 3/1997 |
| GB | 2218831 | 11/1989 |
| GB | 2225637 | 6/1990 |
| WO | WO-8501667 | 4/1985 |
| WO | WO-90/00367 | 1/1990 |
| WO | WO-9109374 | 6/1991 |
| WO | WO-93/01489 | 1/1993 |
| WO | WO-9302622 | 2/1993 |
| WO | WO-9416774 | 8/1994 |
| WO | WO-95/09386 | 4/1995 |
| WO | WO-95/20199 | 7/1995 |
| WO | WO-9522131 | 8/1995 |
| WO | WO-9529447 | 11/1995 |
| WO | WO-96/07908 | 3/1996 |
| WO | WO-96/25877 | 8/1996 |
| WO | WO-9636923 | 11/1996 |
| WO | WO-97/08605 | 3/1997 |
| WO | WO-97/12544 | 4/1997 |
| WO | WO-9737738 | 10/1997 |
| WO | WO-98/16895 | 4/1998 |
| WO | WO-9831275 | 7/1998 |
| WO | WO-9839933 | 9/1998 |

OTHER PUBLICATIONS

"Central Fetal Monitoring Systems ewith Optical Disk Storage", *New Technology Brief*, (Nov./Dec. 1988), vol. 2, No. 6, pp. 249-251.

"European Search Report", From 6858P005EP,(Mar. 27, 1998).

Albisser, A. M., "Intelligent Instrumentation in Diabetic Management", *CRC Critical Reviews in Biomedical Engineering*, vol. 17, No. 1, pp. 1-24.

Anonymous, "Health Hero network, inc. Receives First-Ever FDA Clearance for Connecting Medical Devices to Internet", *PR Newswire*, (Dec. 2, 1999),3 pages.

Billiard, A., et al., Telematic Transmission of Computerized Blood Glucose.

Profiles for IDDM Patients, *Diabetes Care*, (Feb. 1991),vol. 14, No. 2, pp. 130-134.

Bower, "Brain Clues to Energy-efficient Learning", *Science News*, (Apr. 1992),v 141; p215(1); Dialog: File 647, Acc# 12123949.

Bruce, "Health Hero Network CEO, CNNfn", *Digital Jam*, (Dec. 1, 1999),3 pages.

Bruce, et al., "The Effects of Sympathetic Nervous System Activation and Psychological Stress . .", *Diabetologia*, (1992),. ; ; 35 (9); 835-843; Dialog: File 5, Acc# 9629427.

Brunetti, P., et al., "A Simulation Study on a Self-Tuning Portable Controller of Blood Glucose", *The International Journal of Artifical Organs*, (1993),vol. 16, No. 16, pp. 51-57.

Caprihan, A., et al., "A Simple Microcomputer for Biomedical Signal Processing", *IECI '78 Annual Conference Proceedings on Industrial Applications of Microprocessors*, (Mar. 20, 1978),18-23.

Cheng, Joe H., "PCT Search Report", (Jan. 11, 1996).

Douglas, A. S., et al., "Hand-Held Glucose Monitor and Recorder", *Proceedings of the Annual International Conference of the IEEE Engineering in Medicine and Biology Society*, New Orleans, LA,(Nov. 1988),pp. 747-748.

Fabietti, P. G., et al., "Wearable System for Acquisition, Processing and Storage of the Signal from Amperometric Glucose Sensors", *The International Journal of Artificial Organs*, (1991),vol. 14, No. 3, pp. 175-178.

Finston, "Parent + Teacher = Healthy Child", *Diabetes Forecast*, (Apr. 1994),v47 n9; P26(5); Dialog: file 149, Acc# 15804228.

Fox, "Not My Type: Type B Behavior, Type I Diabetes Plus Stress Equals Blood Sugar Blues", *Health*, (Mar. 1988),v20 n3; pp. 22(1); Dialog: File 149, Acc# 06397959.

Frieberger, Paul, "Video Game Takes on Diabetes Superhero "Captain Novolin" Offers Treatment Tips", *San Francisco Examiner*, (Jun. 26, 1992),Fourth Edition, Business Section B1.

Giufrida, Antonio, et al., "Should We Pay the Patient? Review of Financial Incentives to enhance Patient compliance", *Biomedical Journal*, (1997),vol. 315, pp. 703-707.

Hauben, Jay R., "A Brief History of the Cleveland Free-Net", *available at* http://www.asis.org/~irh/acn7-1.a09.html, (1995),pp. 1-4.

Hauser, Thomas, et al., "Will Computers Replace or Complement the Diabetes Educator?", *The Medical Journal of Australia*, (Oct. 5, 1992),vol. 157, 489-491.

Horio, Hiroyuki, et al., "Clinical Telecommunication Network System for Home Monitoring", *Medical & Biological Engineering & Computing*, (Mar. 1994),vol. 32, 227-230.

Hunter, "Technological Advances in Bedside Monitoring: Biosensors", *Archives and Laboratory Medicine*, (Jul. 1987),pp. 633-636.

Kauffmann, Francine, et al., "Epidermiological Study of the Genetics and Environment of Asthma, Bronchial Hyperresponsiveness and Atopy", *Am. J. Respir. Crit. Care Med.*, (1997),vol. 156, pp. S123-S129.

Kuykendall, V G., et al., "Assessment of Self-Monitored Blood Glucose results Using a Reflectance Meter with Memory and Microcomputer", *Symposium on Computer Applications in Medical Care*, (Jan. 1981),vol. 70, pp. 98-102.

Lacyk, John, "PCT Search Report", (Jun. 12, 1997).

Latman, N. S., "Evaluation of Electronic, Digital Blood Glucose Monitors", *Biomedical Instrumentation and Technology*, (1991),vol. 25, No. 1, 43-49.

Laughton, Miles E., "A Portable Microcomputer for Long-Term Physiological Monitoring in the Home and Work Environment", *Medical Monitoring in the Home and Work Environment*, (1990),pp. 47-57.

Leyerle, Beverly J., et al., "The PDMS as a Focal Point for Distributed Patient Data", *International Journal of Clinical Monitoring and Computing*, (1988),vol. 5, pp. 155-161.

Makikawa, M., et al., "Microprocessor-Based Memory Device for Ambulatory Heart Rate and Physical Activity Recording", *Methods of Information in Medicine*, (1994), vol. 33, No. 1, pp. 94-96.

Marsh, David G., "Approaches Toward the Genetic Analysis of Complex Traits Asthma and Atopy", *Am. J. Respir.Crit.Care Med.*, (1997),vol. 156, pp. S-133-S138.

Martinez, Fernando D., "Complexities of the Genetics of Asthma", *Am. J. Respir. Crit. Care Med.*, (1997),vol. 156, pp. S117-S122.

Mazzola, et al., "Video Diabetes: A Teaching Tool for Children with Insulin-Dependent Diabetes", *Proceedings—7th Annual Symposium on Computer Applications in Medical Care; Washington, DC; Dialog:*, (Oct. 1983),File 8, Acc# 01624462.

Meissner, et al., "Building an Integrated Clinical and Research Network", *Proceedings of the SPIE*, (Oct. 24, 1995),vol. 2618, p. 92 99.

Moore, "New Applications Break Through Storage Boundaries", *Computer Technology Review*, (Oct. 1999),vol. 19, No. 10, p. 1.

Pfeiffer, E. F., "The Glucose Sensor: The Missing Link in Diabetes Therapy", *Hormone and Metabolic Research*, (1990),vol. 24, Suppl., pp. 154-164.

Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit".

*Diabetologia*, (1993),vol. 36, pp. 658-663.

Potter, David, "Fundamentals of PC-Based Data Acquisition", *SENSORS*, (Feb. 1994),pp. 12-20.

Reis, Howard, "Telemedicine: Transmitting Expertise to the Point of Care", *Proceedings: Toward an Electronic Patient Record*, (1997),pp. 248-256.

Roberts;, "Diabetes and Stress: A Type A Connection?", *Psychology Today*, (Jul. 1987),v. 21; pp. 22(1); Dialog: File 149, Acc# 05038381.

Rose, V. L., et al., "Decentralized Testing for Prothrombin Time and Activated Partial Thromboplastin Time Using a Dry Chemistry Portable Analyser", *Archives of Pathology and Laboratory Medicine*, (Jun. 1993),vol. 117, pp. 611-617.

Schenkels, P., "Supplementary European Search Report", Application No. EP 97 92 2716,(Mar. 11, 2002).

Schork, Nicholas J., "Genetics of Complex Disease", *Am. J. Respir. Crit. Care Med.*, (1997),vol. 156, pp. s103-S109.

Schrezenmeir, J., et al., "Computer Assisted Insulin Dosage Adjustment-Perspective for Diabetes Control", *Hormone and Metabolic Research Supplement Series*, (1990),vol. 24, pp. 116-123.

Shandle, Jack, "Who Will dominate the desktop In the 90s?", *Electronics*, (Feb. 1990),pp. 48-50.

Shults, Marc C., et al., "A Telemetry-Instrumentation System for Monitoring Multiple Subcutaneously Implanted Glucose Sensors", *IEEE Transactions on Biomedical Engineering*, (Oct. 1994),vol. 41, No. 10, pp. 937-942.

Soeldner, J. S., "Treatment of Diabetes Mellitus by Devices", *The American Journal of Medicine*, (Jan. 1981),vol. 70, 183-194.

Updike, Stuart J., et al., "Laboratory Evaluation of New Resusable Blood Glucose Sensor", *Diabetes Care*, (Nov./Dec. 1988),vol. 11, No. 10, pp. 801-807.

Vallera, D. A., et al., "Accuracy of Portable Blood Glucose Monitoring", *American Journal of Clinical Pathology*, (1991),vol. 95, No. 2, pp. 247-252.

Voelker, Rebecca, "Shoe Leather Therapy is Gaining on TB", *Jama*, (Mar. 13, 1996),vol. 275, 743.

Wyatt, J. C., "Clinical Data Systems, Part 2: Components and Techniques", *Lancet*, (Dec. 1994),vol. 344, No. 8937, pp. 1609-1614.

Yoshizawa, Daisuke, et al., "The Development of a Data Processing System with Perosnal Acomputer of MSX Standard System for Flow Injection Analysis", *Journal of Flow Injection Analysis*, (1988),vol. 5, No. 2, pp. 101-110.

"AdOptimizer-ad Management Software For Websites", Newsbytes, pNEW10040041, Oct. 4, 1996.

"Cathay Pacific Airways-USA receives more than 1,300 bids during first five days of CyberAuction"; Business Wire, Oct. 18, 1995, p10181119.

"Cathay Pacific Airways-USA to Hold First-Ever Internet CyberAuction; CyberTravelers Can Bid for 50 Business Class Round Trips to Hong Kong-No Minimum Bid"; Business Wire; p9261084; Sep. 26, 1995; DIALOG: File 148, Acc#08167091.

"European Search Report", From 6858P005EP, (Mar. 27, 1998).

"Who Will Dominate The Desktop in the 90's?", Jack Shandle, Electronics, Feb. 1990, pp. 48-50. (3 pages) Cited by 2 patents.

Adilman; "Videogames: Knowing the Score"; Creative Computing; v9; p. 224(5); Dec. 1983; Dialog: File 148, Acc#01891055.

BAI, "design of home healthcare network", IEEE 1997 pp. 1657-1658.

Brenman et al.; "Interaction of Nitric Oxide Synthase with the Postsynaptic Density Protein PSD-95 and α1-Syntrophin Mediated by PDZ Domains"; Cell; vol. 84, pp. 757-767, Mar. 8, 1996; Ref: XP-002104701.

Edelson; "Fashion Reevaluates Flickering Fortunes of TV Home Shopping"; WWD; v170 n87; p. 1(3); Nov. 8, 1995; DIALOG: File 148, Acc#08289119.

Franklin; "Proposed Auction Rules for PCS: The FCC Plans to Use Competitive Bidding, but Exact Procedures are Undefined"; Cellular Business; v10 n13; p. 18(2); Dec. 1993; DIALOG: File 148, Acc#06787310.

Furnham, et al; "Measuring Locus of Control: a Critique of General Children's Health- and Work-related Locus of Control Questionnaires"; British Journal of Psychology; v84 n4; p. 443(37); Nov. 1993; Dialog: File 88, Acc# 14903135.

Gardener, et al.; "Comprehension and Appreciation of Humorous Material Following Brain Damage"; Brain; Sep. 1975; 98(3); pp. 399-412; Dialog: File 153, Acc#02859983. (14 pages).

Gordon; "Auctions Become High Tech"; Dealer Business; v29 n7; p. 21(4); Mar. 1995; DIALOG: File 148, Acc#07862519.

Howey, et al., "A rapidly Absorbed Analogue of Human Insulin"; Diabetes, vol. 43, Mar. 1994, pp. 396-402. (7 pages).

Hutheesing, Nikhil, "An on-line gamble", Forbes, v157 n10 p. 288(1), May 20, 1996.

Jaffrey et al.; "PIN: An Associated Protein Inhibitor of Neuronal Oxide Synthase"; Science; vol. 274; Nov. 1, 1996; Ref: XP 002050141.

Jimison et al., "Patient-Specific explanation in models of chronic disease", Revised Feb. 1992 Artificial intelligence in Medicine 4 (1992) 191-205.

Jones, Chris, "Microsoft readies DocObject; technology will allow document editing in Web browsers", InfoWorld, v18 n18 p. 48(1), Apr. 29, 1996.

Kennedy et al.; "Television Computer Games: A New Look in Performance Testing"; Aviat Space Environ Med; Jan. 1982, 53(1); pp. 49-53. (5 pages); Dialog Abstract: File 155, Acc#0353751.

Lachnit, Carroll, "Hawkin's Online Auction", Photo District News, vol. 16, Issue 1, p. 18, Jan. 1996.

Luebke, Cathy, "Barrett-Jackson Auction Turns High-Tech", Business Journal, vol. 16, Issue 12, pp. 11, Jan. 19, 1996.

Marx, Wendy, "More than just the Scores: ESPNET SportsZone is a model for expanding brand names online", InformationWeek, n576 p. 61(2), Apr. 22, 1996.

McCullagh, PJ et al., "Computerized paradigms for eliciting the contingent negative variation event-related potential," Proceedings of the Annual International Conference of the Engineering in Medicine & Biology Society, IEEE, Conf. 14, p. 2481-2483, Oct. 1992.

Miles, Laughton E., "A Portable Microcomputer for Long-Term Physiological Monitoring in the Home and Work Environment", Medical Monitoring in the Home and Work Environment, (1990), pp. 47-57.

Mims; "Psychological Testing"; Computers & Electronics; v23; p. 22(6); Feb. 1985; Dialog: File 47, Acc# 2654858.

Research project launched to improve health of America's communities; new Disney community in Florida is focus of program. Business Wire, p10011142. Oct. 1, 1996.

Schement, "An Intelligent Controller for Neurophysiological Experiments," Proceedings of the Annual Symposium on Computer Based Medical Systems, Durham, Jun. 14-17, 1992, p. 528, line 1—p. 529, line 21.

Siegmann;"Nowhere to Go but Up"; PC Week; v12 n42, p. A5(1); Oct. 23, 1995; DIALOG: File 148, Acc#08222496.

Skolnick et al. "Simultaneous Analysis of Multiple Polymorphic Loci Using Amplified Sequence Polymorphisms (ASPs)"; Genomics. 2: 273-279.

Spitzer et al.; "The moderating effect of age on self-care"; Western Journal Of Nursing Research, v18, n2, p136(13), Apr. 1996.

Telemedicine Provides Two-Way Computer Link For Parents of Very Premature Infants. PR Newswire. p1007NEM034. Oct. 7, 1996.

United Healthcare's OPTUM Division goes online to better health by announcing a unique internet application. PR Newswire, p0801MNTH004. Aug. 1, 1996.

Valla, et al., "A Structured Pictorial Questionnaire to Assess DSM-III-R-based Diagnosis in Children (6-11 years)"; Journal of Abnormal Child Psychology; v22 n4; p. 403(21); Aug. 1994; Dialog: File 88, Acc# 15759542.

Wilkins, Aaron. "Expanding Internet access for health care consumers", Health Care Management Review, Summer, Jul. 24-30, 1999.

* cited by examiner

| | Luna, Craig | HEALTH HERO |
| --- | --- | --- |
| Find Patient [GO] | Fri, April 4, 2003 | NETWORK |
| (Last Name) | ▷ Contact Health Hero  ▷ Help  ▷ Log Out | |

| Home | Patient | Reports | Enrollment | Disenrollment | Schedule | Setup |
| --- | --- | --- | --- | --- | --- | --- |
| Work List | Profile | Results | Trends | Notes | | |

Use these options to change the work list below.

1. Show patients from which program?  2. For which session date?  3. For which care management?

[------ All Programs ------ ▽]   [11/19/2003 ▽]   [-- All Care Managers -- ▽]

Printer friendly version                    [Create Work List]

You are viewing sessions for Nov 19, 2003 in the "All Programs" Program    Date: ◁ ▷

| Responders' Risk Summary | | | | |
| --- | --- | --- | --- | --- |
| | Symptoms | Behavior | Knowledge | General |
| High Risk | 2 | 2 | 0 | 0 |
| Medium Risk | 0 | 1 | 2 | 0 |
| Low Risk | 6 | 5 | 4 | 2 |
| None | 0 | 0 | 0 | 6 |

| Patient Summary | |
| --- | --- |
| Responders | 8 |
| Non-Responders | 4 |

| Responses on Monday, November 19, 2003 | | | | | |
| --- | --- | --- | --- | --- | --- |
| Patient | Response Time | Sympt. | Bhvr. | Kwldg. | Gen. |
| ● Lang, Nancy | 08:38 AM PST | High | High | | Low |
| ● Cherry, Julie C. | 08:41 AM PST | High | Low | Low | None |
| ● Beninger, Jennifer | 11:15 AM PST | Low | High | Medium | None |
| ◒ Messing, Mel | 10:16 PM PST | Low | Medium | | None |
| ○ Lapp, Mary | 09:38 AM PST | Low | Low | Medium | None |
| ○ Coll, Laurie | 10:09 PM PST | Low | Low | Low | None |
| ○ Hoff, Jane | 11:14 AM PST | Low | Low | Low | Low |
| ○ Man, Marie | 09:12 AM PST | Low | Low | Low | None |

Back to Top

FIG. 6

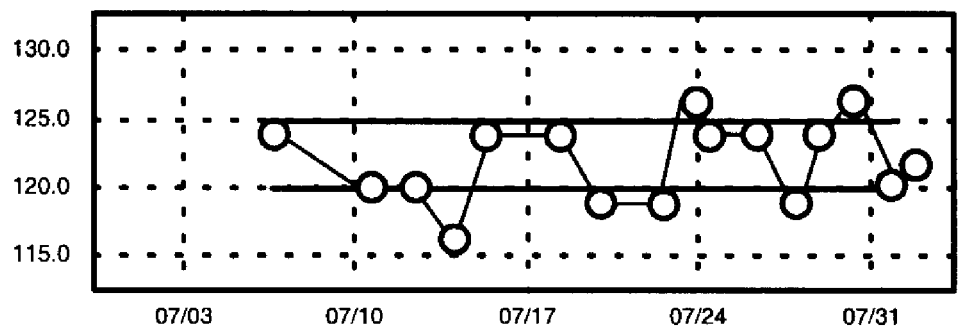
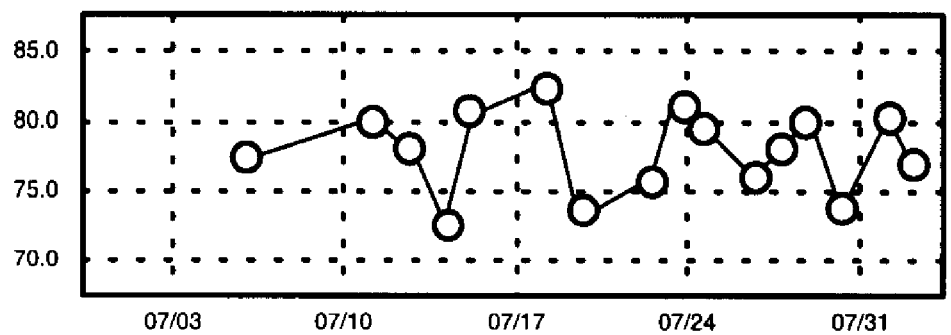
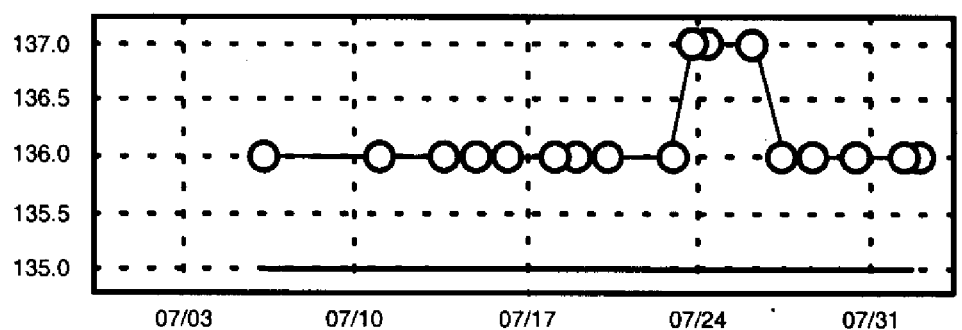
FIG. 7

A 3-DIMENSIONAL MODEL OF DISEASE

AGENDA

- ▨ HEALTH HERO NETWORK BACKGROUND
- ▨ CURRENT TECHNOLOGY SOLUTIONS
- ▨ CONTRIBUTION TO MEDKNOWLEDGEMENT
  - INFORMATION AND KNOWLEDGE ACQUISITION → THE FEEDBACK LOOPS
  - CONTRIBUTION TO INNOVATIONS
  - LINKAGE TO OTHER PARTS OF PROJECT
  - PATIENT TRIALS AND EXPECTED OUTCOMES

FIG. 14

HEALTH HERO NETWORK VISION

- ▨ A BETTER MODEL OF CARE IS POSSIBLE
- ▨ CRISIS CARE → COORDINATED CARE
- ▨ eHEALTH NETWORKS AND TECHNOLOGIES = A POWERFUL ENABLER

FIG. 15

HEALTH HERO NETWORK

- FOUNDED 1988 IN MOUNTAIN VIEW, CALIFORNIA. HEALTH HERO NETWORK LTD ESTABLISHED 2003 IN DUBLIN, IRELAND.

- 25 EMPLOYEES, $5 MILLION ANNUAL SALES, SERVING 30 PROVIDER SITES AND 2500 PATIENTS WITH DAILY IN-HOME MONITORING.

- SOLUTION PARTNERS SIGNED IN IRELAND, FRANCE, NETHERLANDS. EXPECTING TO ADD SPAIN, BELGIUM, NORWAY IN 2003.

- LICENSEES INCLUDE VETERANS HEALTH AFFAIRS, MERCY HEALTH SYSTEM, AMERICAN MEDICAL ALERT, THERASENSE, PHILIPS.

FIG. 16 eHEALTH DEMONSTRATION:
VETERANS HEALTH AFFAIRS (US)

- CHRONIC CARE PROGRAM USING MODEL OF CARE BASED ON eHEALTH NETWORKS AND TECHNOLOGIES FROM HEALTH HERO NETWORK

- 791 ELDERLY HIGH-RISK PATIENTS WITH HYPERTENSION, HEART FAILURE, COPD, DIABETES, ENROLLED FOR 1 YEAR, COMPARED TO COMPARISON GROUP DATA

- RESULTS (DISEASE MANAGEMENT, VOLUME 5, NUMBER 2, 2002)
  - 63% REDUCTION IN HOSPITAL ADMISSIONS
  - 60% REDUCTION IN HOSPITAL BED DAYS
  - 40% REDUCTION IN EMERGENCY ROOM VISITS
  - 64% REDUCTION IN NURSING HOME ADMISSIONS
  - 88% REDUCTION IN NURSING HOME BED DAYS
  - SIGNIFICANT IMPROVEMENT IN QUALITY OF LIFE

FIG. 17 eHEALTH DEMONSTRATION:
MERCY HEALTH SYSTEM (US)

- DIABETES MANAGEMENT PROGRAM USING eHEALTH NETWORKS AND TECHNOLOGIES FROM HEALTH HERO NETWORK

- 169 LOW INCOME DIABETES PATIENTS, ONE YEAR STUDY PERIOD USING COMPARATIVE COHORT DATA FROM PREVIOUS CALENDAR YEAR

- RESULTS (DISEASE TECHNOLOGIES & THERAPEUTICS JOURNAL, DEC 2002)
  - OUTPATIENT VISITS REDUCED 49% ($p<0.001$)
  - INPATIENT ADMISSIONS REDUCED 32% ($p<0.07$)
  - ER ENCOUNTERS REDUCED 34% ($p<0.06$)
  - SIGNIFICANT INCREASE IN QUALITY OF LIFE SCORES
  - MEDICATION COMPLIANCE INCREASED FROM 34% TO 94%

FIG. 18

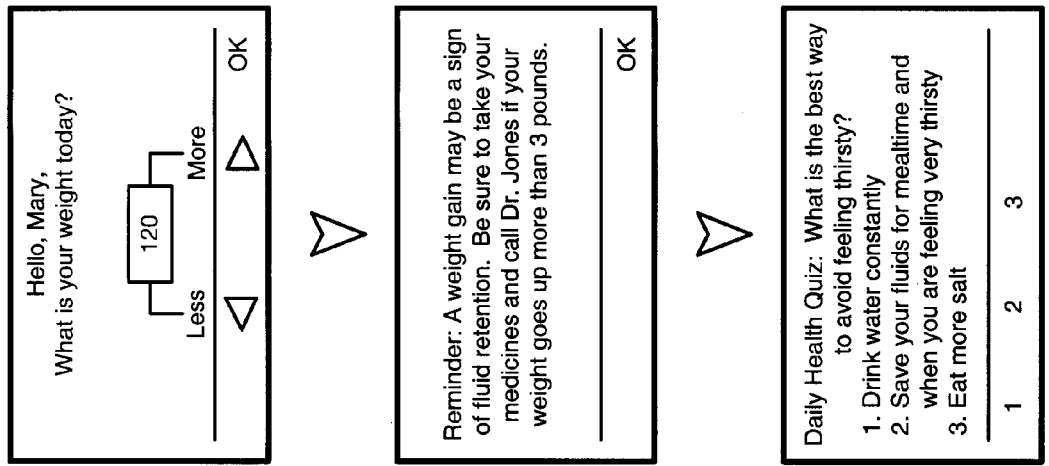
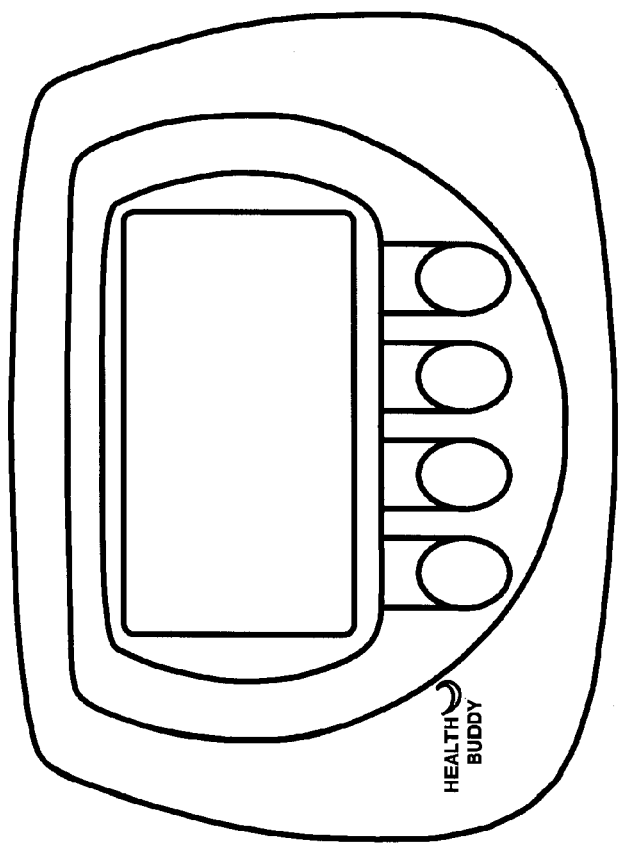
DAILY DIALOGUE WITH THE PATIENT
VISION: INTELLIGENT, INTERACTIVE, PERSONALIZED, SIMPLE, INTEGRATED WITH CONSUMER AND MEDICAL DEVICES
FIG. 21

PATIENT DIALOGUE CONTENT

VISION: BASED ON LATEST MEDICAL KNOWLEDGE, INDIVIDUALIZED, GENERATING REAL-TIME INFORMATION

Demo Library / Demonstration day dialogues
Diabetes Day — Health Hero NETWORK ...u may start at any time.
lood sugar trend question:
thing to eat for 8 hours or
ms]
lood sugar? (Please use the
ar) [BS Value trend: Blood sugar
d sugar under 70 is considered
Remember to eat a sugar source
r is low, take your medicine,
als and snacks as
y your doctor. [Response: Blood
/ Symptoms]
d sugar between 131-239 is
ered to be moderately high.
ke your insulin or diabetic pills
our doctor. [Response: Blood
/ Symptoms]
r doctor if you continue to have
r levels for 3-4 days. [response,
r monitoring / Symptoms]
r over 240 is generally
e too high. Remember to take

Demo Library / Demonstration day dialogues
COPD Day — Health Hero NETWORK for you! You may start at any
COPD, so that you can take the
sease process / knowledge]
s and symptoms: Disease process 3 days? [More S&S: None / report this to your doctor today.

our doctor's instructions.
s]

ng your doctor's instructions.

structions to keep up your health.

ction are fever, coughing up
reath. [Lung infection: Pulmonary / more shortness of breath than
Acknowledge: Pulmonary / or having more shortness of
infection. [Instruct: Pulmonary /

Demo Library / Demonstration day dialogues
CHF Day, 0101 — Health Hero NETWORK Legend: 0=No Risk  @=Low Risk  &=Medium Risk  #=High Risk ?Welcome back, Pat! Thank you for using the Health Buddy. Begin whenever you are ready [Greeting 2: None / General]
?Did you weigh yourself today? [Did you weigh today?: Weight / Behavior]
　@Yes
?What is your weight today? (Use the arrows to indicate your weight)[Weight trend: Weight / Symptoms]
?(Q[Weight trend]>(M[High Weight]+2))
　0 True
　　?This is much higher than your usual weight. Sometimes weight can be affected by heavy clothing or shoes. Please be sure that you weighed yourself without heavy clothing or shoes. [Much higher: Weight / Symptoms]
　　　#Okay
　　?Remember, if your weight is up 3 or more pounds, call Dr. Welby today at 555-1212. [Reminder: Weight / Symptoms]
　0 False
　　?:(Q[Weight trend] = (M[High Weight]+2))
　　　0 True
　　　　?This is somewhat higher than your usual weight. Sometimes weight can be affected by heavy clothing and shoes. Please be sure that you weighed yourself without heavy clothing or shoes. [Somewhat higher: Weight / Symptoms]
　　　　　&Okay
　　　?(Q[Weight trend]=(M[High Weight]+1))
　　　　0 True
　　　　　?This is slightly higher than your usual weight. Sometimes weight can be affected by heavy clothing and shoes. Please be sure that you weighed yourself without heavy clothing or shoes. [Slightly higher: Weight / Symptoms]
　　　　　　@Okay

FIG. 22

HEALTH HERO NETWORK CONTRIBUTION TO MEDKNOWLEDGEMENT

- ▨ 1.1 INFORMATION AND KNOWLEDGE SOURCES AND FORMATS
- ▨ 1.2 INFORMATION ACQUISITION → INFORMATION BASE
- ▨ 1.3 KNOWLEDGE ACQUISITION → KNOWLEDGE BASE
- ▨ 1.4 INFORMATION AND KNOWLEDGE PROCESSING → DSTs TO IDENTIFY GAPS BETWEEN INFORMATION BASE AND KNOWLEDGE BASE (I.E., GAPS BETWEEN WHAT IS AND WHAT SHOULD BE)
- ▨ 1.5 INFORMATION AND KNOWLEDGE RENDERING → RENDERING ENGINE IS THE INTERFACE TO END USERS

---
▨ 1.6 INFORMATION AND KNOWLEDGE ACQUISITION → THE FEEDBACK LOOPS

INFORMATION AND KNOWLEDGE ACQUISITION → THE FEEDBACK LOOPS

- ▨ PATIENT DIALOGUE ENGINE: INDIVIDUALIZED COMMUNICATION
  - → GENERATED USING INFORMATION AND KNOWLEDGE BASE
  - → INTERFACE WITH RENDERING ENGINE
  - → FEEDBACK TO INFORMATION BASE
- ▨ CARE MANAGEMENT ENGINE: JUST-IN-TIME CARE
  - → GENERATED USING INFORMATION AND KNOWLEDGE BASE
  - → FEEDBACK TO DSTs
- ▨ RESEARCH ENGINE: REAL-TIME RESEARCH
  - → INTERFACE TO INFORMATION BASE [EXTRACT EXISTING DATA]
  - → INTERFACE TO DIALOGUE ENGINE [WHEN NEW DATA IS REQUIRED]
  - → FEEDBACK TO KNOWLEDGE BASE [NEW DISCOVERIES]

FIG. 24

INTEGRATING FEEDBACK LOOPS WITHIN MEDKNOWLEDGEMENT

- APPLICATION PROGRAM INTERFACES
- STANDARDS FOR DATA CLASSIFICATION
- ONTOLOGY FOR INFORMATION AND KNOWLEDGE USED IN FEEDBACK PROCESS

A 3-DIMENSIONAL MODEL OF DISEASE

EXPECTED RESULTS

- ▨ REDUCED EMERGENCY DEPARTMENT ENCOUNTERS AND HOSPITALIZATIONS BY DETECTING PATIENT PROBLEMS BEFORE THEY BECOME A CRISIS

- ▨ IMPROVED PATIENT COMPLIANCE BY EDUCATING, MOTIVATING AND MONITORING HEALTH STATUS AND BY PROVIDING PERSONALIZED AND RELEVANT INFORMATION

- ▨ IMPROVED SAFETY AND QUALITY OF CARE BY PROVIDING TIMELY AND ACTIONABLE INFORMATION TO HEALTHCARE PROFESSIONALS THROUGH QUALITY ASSURED PROCESSES THAT CAN BE CONTINUOUSLY IMPROVED

- ▨ CONTINUITY OF CARE, PARTICULARLY FOR THE ELDERLY, THROUGH INTEGRATED, INTERCONNECTED MONITORING AND INFORMATION SYSTEMS, RATHER THAN FRAGMENTED, EPISODIC, AND CRISIS DRIVEN CARE

FIG. 28

METHOD AND SYSTEM FOR INTEGRATING FEEDBACK LOOPS IN MEDICAL KNOWLEDGE DEVELOPMENT AND HEALTHCARE MANAGEMENT

This application claims the priority of U.S. Provisional Application No. 60/461,105 filed Apr. 7, 2003 and U.S. Provisional Application No. 60/461,526 filed Apr. 8, 2003, both of which are incorporated herein by reference.

FIELD OF THE INVENTION

E-health technologies are enabling a shift in the paradigm of health care from a model overly devoted to episodic, crisis-driven care toward a model characterized by continuity, crisis prevention, citizen empowerment, and ubiquitous monitoring and management of health and lifestyle factors outside of the traditional patient encounter.

This paradigm shift is generating new opportunities and demands to advance and disseminate medical knowledge toward truly individualized care, yet new tools are needed before such advances can be integrated into clinical practice and be made available to citizens. The need for new tools is particularly acute—and the opportunity particularly large—in chronic care, where the need for care is increasing due to the aging population while the supply of caregivers is declining.

BACKGROUND OF THE INVENTION

This proposal research and develop of a comprehensive new methodology and tool set for medical knowledge management, dissemination, and individualization. The research and development activities include (1) development of an ontology and semantics engine for medical knowledge and patient information from diverse and heterogeneous sources in order to determine best practices and consensus standards of care on a continuous basis, (2) development of decision support and knowledge dissemination tools in order to generate timely, relevant, and individualized care plans and patient education, and (3) development of a continuous feedback methodology and system whereby data gathered from the citizen enables care providers to automatically individualize care plans and patient communications and medical researchers to continuously test and validate rules and associations that drive that individualization.

Additionally, tools will be developed to enable researchers to identify patient characteristics that correlate to disease progression and outcomes and study of disease based on far more detailed patient data, collected at far higher frequency, and on a larger scale than was previously possible. The vast new amounts and sources of data, particularly high frequency data from ubiquitous monitoring outside of the traditional encounter necessitates the development of a new generation of knowledge management tools that automate and integrate the collection, processing and dissemination of medical knowledge to a greater degree than has previously existed.

As these e-health care management tools are disseminated and introduced into clinical practice and medical research, it will become possible for care providers, patients, and researchers to better understand, predict, prevent, and manage disease. The overall goal is to apply and generate medical knowledge in a continuous dynamic feedback process that leads to the lowest achievable risk and cost to society and the highest quality of care and quality of life for citizens.

SUMMARY OF THE INVENTION

In one embodiment, a system for processing medical knowledge, includes a system a database of medical knowledge sources, wherein an ontology specifies how the medical knowledge sources apply to specific disease conditions and patient populations; a rendering engine to convert medical a rendering engine to convert medical knowledge obtained from the medical knowledge sources to a format suitable for a presentation to a patient on a selected patient device; and a feedback engine to receive feedback from a plurality of patients and to provide feedback data to the database and the knowledge sources.

BRIEF DESCRIPTION OF THE DRAWINGS

An embodiment of the present invention is illustrated by way of example and not limited in the figures of the accompanying drawings, in which like references indicate similar elements and in which:

FIG. 6 is a user interface diagram illustrating the Patient Work List in accordance to an exemplary embodiment of the present invention;

FIG. 7 is a chart diagram illustrating the patient data in accordance to an exemplary embodiment of the present invention;

FIGS. 14-28 are diagrams summarizing one exemplary embodiment of the present invention.

DETAILED DESCRIPTION

Figure 1:
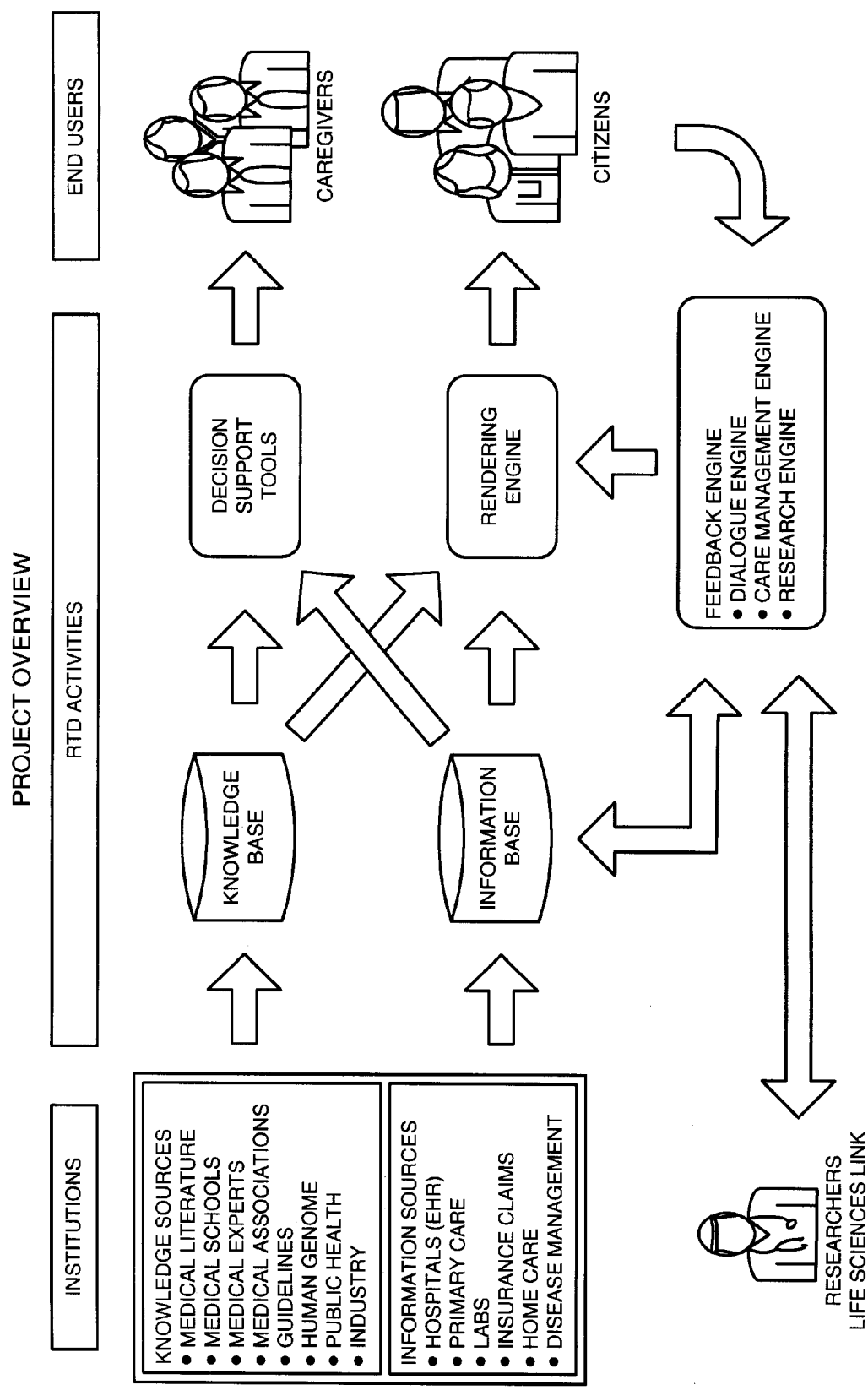
FIG. 1 is an overview diagram of the system, according to an exemplary embodiment of the present invention.

Proposed Project:

In view of the above, MedKnowledgeMent aims to provide the methodology and tools for implementing a comprehensive knowledge management strategy in the medical environment, with the capability to encompass, classify, process and deliver the necessary information at the appropriate time.

FIG. 1.

The proposed project will include—

I. In Formation and Knowledge Sources—

Relationships will be established with sources of medical knowledge, including Universities, Medical Schools, Hospitals, Clinical Laboratories, Primary Care Units, Physicians, Care Managers, Medical Research Facilities, medical literature, and other sources of medical knowledge. There shall be co-ordination with these sources in order to develop the overall system.

II. Knowledge Acquisition—Knowledge Base:

An ontology will be developed for medical knowledge in order to specify how medical knowledge sources apply to specific disease conditions and patient populations. In this ontology, each disease diagnosis will be associated with a set of representational terms covering aspects of care for the condition. Sub categorization under the aspect of care will include available treatments, and conditions upon which such treatments are used. Based on this ontology, a medical knowledge base will be developed from which it will be possible to search for and determine the consensus standards of care based on search criteria. An application program interface (API) and query language will be developed to this knowledge base so that other programs can use the knowledge base to run queries for specific needs in order to determine and derive consensus standards of care in a structured way that can be applied as a rule base a decision support system. For example, a care management program could seek information on the consensus standard of care for frequency of a particular lab test for a particular disease, as in HbA1c tests for a patient with Type II diabetes in a particular age group of patients. Because lab tests for particular diagnosis will be part of the ontology for classification of knowledge in relation to a disease, the methodology will allow such a query. Research and development needs to be done to create a generally applicable ontology and semantic network that will allow a scalable classification of knowledge across a wide range of disease conditions and populations. Interface to this subcomponent will be an API and query language. For this project, care plans will be developed for a range of conditions including Chronic Obstructive Pulmonary Disease, Congestive Heart Failure, Type II Diabetes Mellitus, End Stage Renal Disease/Transplant, and Depression.

III. Information Acquisition—Information Base:

An ontology and query language will be developed in order to extract data from existing clinical information systems including Electronic Health Records (EHR), Laboratory Databases, Medical Claims Databases, Genetic and Molecular Biology Databases in addition to patient self-reported data that is entered via the Internet and self-care devices. Based on this, an Information Base is generated and integrated in real-time.

Semantics Engine will have the capability to integrate patient information from multiple sources of External Data, including electronic health records, laboratory data, medical claims data, genetic and molecular biology data. Semantics Engine references the data available from the external sources, and integrates this data into the patient's Information Base through the use of an API. Data is classified in a standard manner to allow the extraction of necessary elements to compute risk factors for each of the health contexts in the 3-dimensional model of disease for every patient.

The Electronic Health Records (EHR) of a patient is referenced, and information is extracted by the usage of Natural Language Processing Algorithms. The typical information that would be extracted from an ERR includes Patient demographic variables, including name, age, sex, race, national ID number, contact information main diagnosis, co-morbid conditions, chief complaints, physical examination findings, family history, lifestyle related factors, such as a history of smoking, alcohol consumption, exercise frequency of visits to the healthcare facility, referrals to other health providers, including specialists, co-morbid conditions, diagnostic tests ordered, dates of ordering of these tests, and results of the diagnostic tests. Included here are the radiological, nuclear medicine investigations and functional tests such as exercise stress tests.

prescribed medication, response to medication, development of side-effects, especially if the side-effects have necessitated withdrawal of the medication, history of admissions, special procedures (such as operations) undertaken, indications for the procedure Laboratory Data includes data from a diagnostic laboratory—biochemical, pathology, and microbiology, immunological investigations. The data which is of primary concern to the system is the date, and type of test, and the test result. The test results may be used to schedule additional tests through the use of further protocols. For example, if a test value is reported as high, the Care Manager Program institutes an intervention, as indicated by the protocol, in addition to scheduling a follow up laboratory test to check the effectiveness of the protocol in patient care.

Medical Claims Data from the database of an insurer or public health subsidizing organization is extracted by the Semantics Engine and complements the data in the EHR. Medical Claims Data provides information on the dates and nature of procedures, tests and consultations that a patient undergoes. This information is further processed by protocols. For instance, the claims data for a diabetic patient may show that the recent most visit to an ophthalmologist to be 3 years previously, whereas the standard of care requires this to be every 2 years. Care Management Engine alerts the care manager to this fact, and a new consultation is scheduled. Semantic Engine correlates the medical claims data and EHR in order to prevent duplication of data.

Genetic and Molecular Diagnostics Database—Semantic Engine extracts a patient's genetic and molecular profile from a Genetics Database, and incorporates this information within Information Base. This is used by Care Management Engine to modify the treatment plan of an individual on the basis of his/her molecular and genetic profile. For example, patients with polymorphisms in genes for cytochrome oxidases exhibit a different degree of metabolism, and side effects of antidepressants and tests for cytochrome polymorphisms may be used to determine the best drug to be used in a given patient. Another interesting application is that this data may be used by the research engine to correlate subgroups of patients based on treatment response and disease outcomes (phenotypic variables) to genetic variations including SNP markers and molecular profiles. Many chronic diseases such as diabetes, hypertension, cardiovascular disease, obesity, and mental health disorders are thought to have a genetic component.

IV. In Formation and Knowledge Processing: Decision Support Tools—

Queries will be run on Information Base to correlate the extent to which provided care is consistent with the consensus standard of care—the Knowledge Base. Decision Support Tools (DSTs) will use the results of these queries to generate reports that identify potential gaps in patient care. These 'gaps' in care, the difference between hitherto provided care and the consensus standard care' is summarized, and presented to caregivers, i.e. physicians and care managers. For example, patients with diabetes are required by knowledge base to have an HbA1c test every three months. In cases where DSTs detects that the last such test has been performed more than this interval, a recommendation is given to check if the patient has had an unreported test. If this is the case, then the missing test results are entered into the information base. If not, then the test is performed. In the interest of patient safety and quality assurance, it is necessary that the physician or care manger screens the 'care gap' report and confirms that the gaps are not due to missing data.

V. Information and Knowledge Rendering: Rendering Engine—

Dialogues and health content is rendered for presentation, by a Rendering Engine that converts the data into a format which may be interpreted by different types of devices including Personal Computers connected to the Internet, interactive Television, Personal Digital Assistants, and remote health appliances, such as the Health Buddy™ appliance that are used by a patient to communicate with the system. Conversely, Rendering Engine converts patient replies to dialogs, and biometric measurements from different devices into the standard system format.

VI. Information and Knowledge Acquisition: Feedback Engine—

Figure 2:
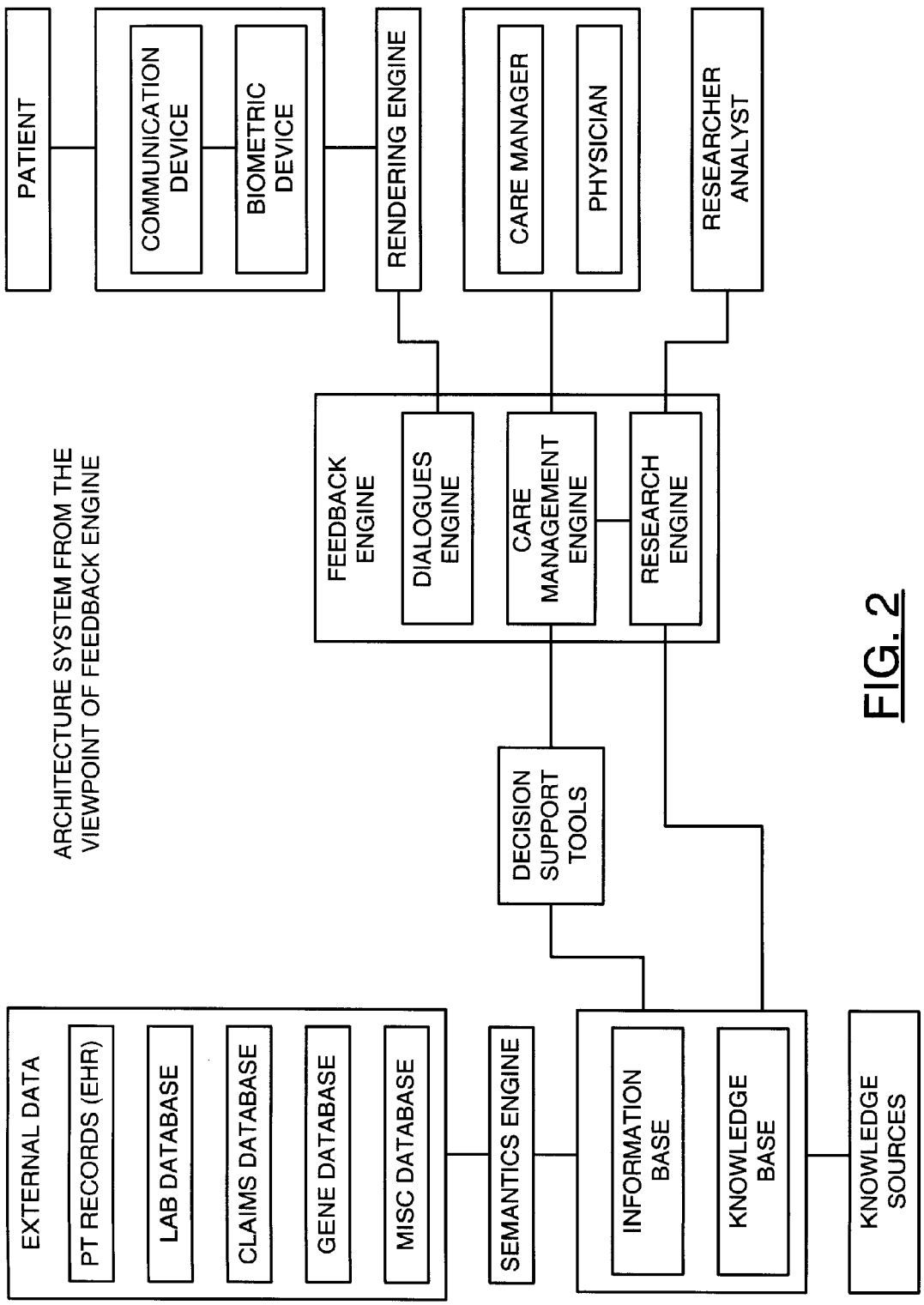
FIG. 2 is a diagram illustrating the system architecture form the viewpoint of a Feedback Engine in accordance to an exemplary embodiment of the present invention.
Figure 3:
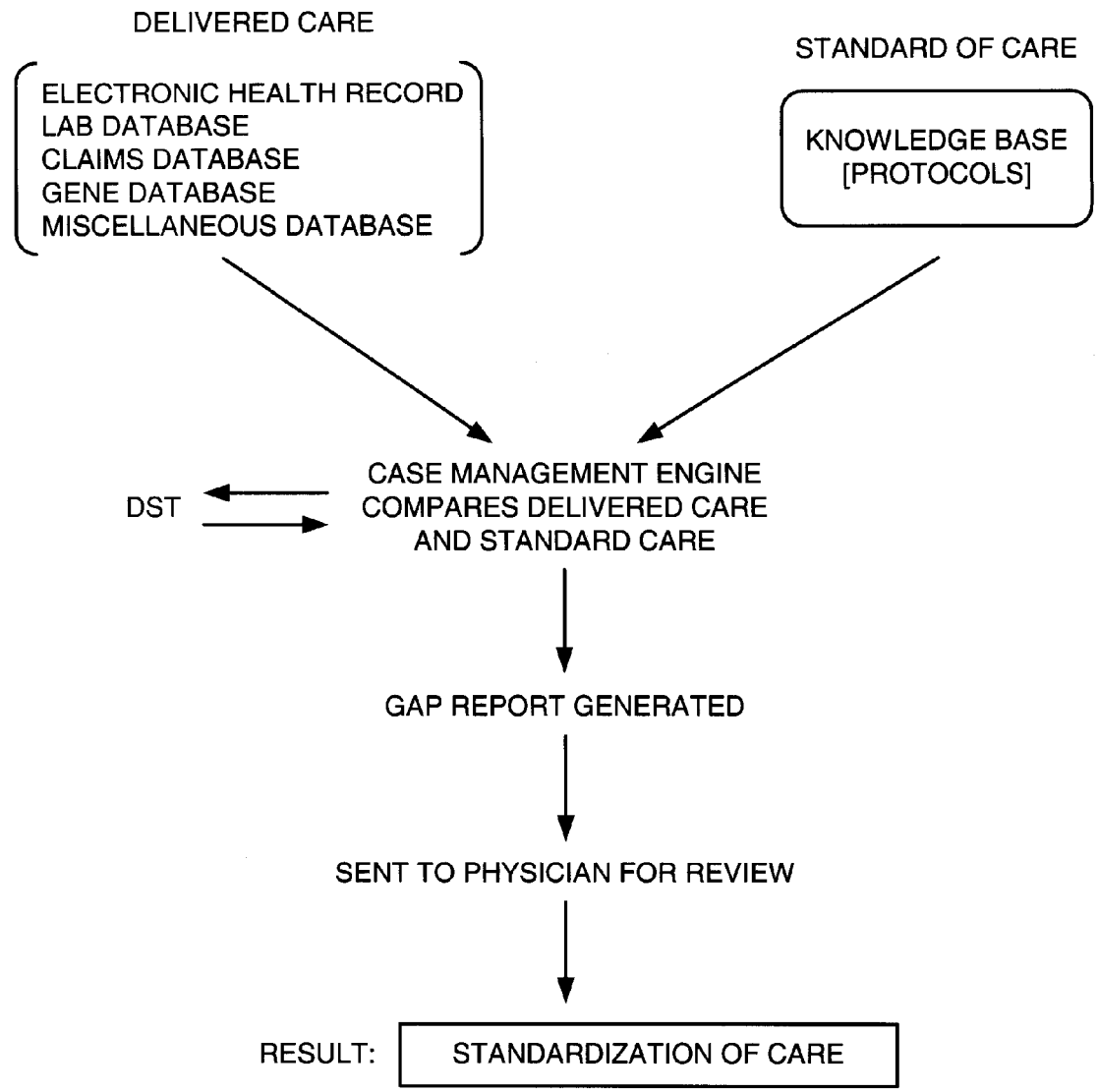
FIG. 3 is a diagram illustrating a Care Management Engine interface with a DSTs to provide gap reports in accordance to an exemplary embodiment of the present invention.
Figure 4:
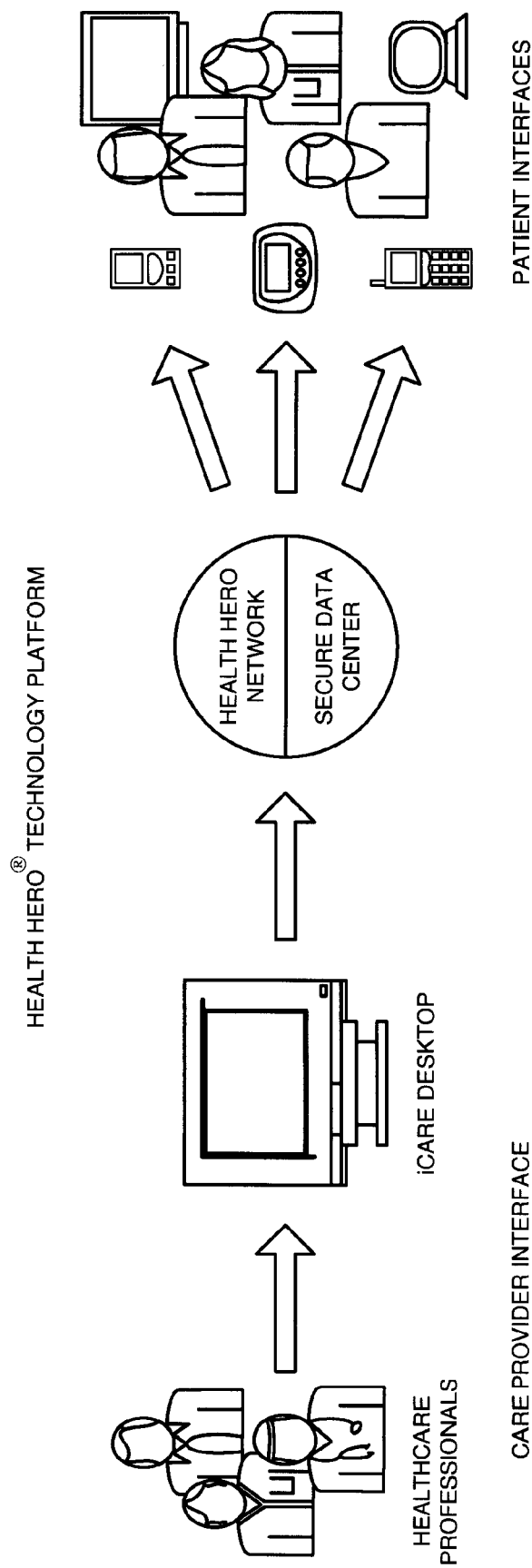
FIG. 4 is a diagram illustrating the technology platform in accordance to an exemplary embodiment of the present invention.
Figure 5:
FIG. 5 is a user interface diagram illustrating the Inbox of a care provider in accordance to an exemplary embodiment of the present invention.

The Feedback Engine is of key importance in the knowledge management cycle. Feedback Engine will enable a regular and ongoing interaction between the patient and the care manager, physician and researcher, outside of the clinical encounter. Feedback Engine will interface with DSTs using Application Program Interfaces, to generate personalized recommended 'care plans' based on the patient's updated Information Base and disease Knowledge Base. Care plans will be forward looking and will recommend steps for monitoring and managing patients along a future timeline. The structure of the monitoring and management plan is based on the characteristics—symptoms, behavior (i.e. treatment compliance), knowledge and test results matched to medically relevant aspects of care. The plan will include monitoring, management and follow-up directly with the patient and reporting to the care manager. This is an intervention that would be implemented using eHealth technologies for frequent dialogues with the patient over a network. It will also include a customized health education plan. Caregivers, i.e. physicians and care managers decide, in consultation with the patient the future course of action, with regard to the recommended care plan. In the first iteration of the patient monitoring and management plan, the plan is based on the personalization of a pre-packaged care plan designed for the specific medical condition of the patient. Subsequent iterations will allow for progressively greater customization and individualization of plans to the information base. Feedback Engine will allow the system to correlate and analyze data within Information Base and Knowledge Base and apply these analyses to make new discoveries and further the growth of medical science. Feedback Engine will consist of three components—FIG. 2.

a. Dialogue Engine—Dialogue Engine maintains ongoing patient interaction that is individualized to the patient. It sends dialogues (content) to the patient for display on the communication device. Dialogues include medical advice to the patient, educational materials, and queries to a patient regarding his/her medical condition. Dialogues can also be script programs instructing the Biometric Device to collect physiological measurements of the patient. Dialogues are generated using Information and Knowledge Base. Dialogues Engine interfaces with the Rendering Engine in order to customize the dialogues to the specific type of communication and biometric devices used by the patient. Replies to dialogues, and measurements from Biometric Devices are fed back into the Information Base.

b. Care Management Engine—The individual patient data resulting from the monitoring and management plan will be fed back into the Information Base, where it becomes a part of the patient record that is used in subsequent iterations of the Information and Knowledge Processing System to generate an increasingly individualized care plan with as the knowledge base grows and increases in its precision. This will allow the patient care plan to attain a greater degree of patient specificity and individualization with the passage of time, as the system has a better perspective of a patient's specific needs. As the research and development in this project refines the methodology and semantic network for sharing medical knowledge, the feedback loop will be enhanced to enable a transition from personalized 'prepackaged programs' to truly patient specific 'individualized programs'. Care Management Engine may also interface with DSTs in order to provide gap reports, as shown in the FIG. 3 below.

FIG. 3.

c. Research Engine—The data aggregated from the original patient profile in combination with the longitudinal data created from the patient monitoring and management plan will be aggregated across the entire population of patients in the system. Such data will be blinded and no individually identifiable characteristics will be retained. The research engine tool set will enable a researcher to perform a query on a patient population and to identify subgroups of that population with different characteristics. With these clusters, the researcher will then be able to search for any other variable with meaningful correlation to the respective clusters. Examples of searches that will be performed include identifying subgroups of patients who respond differently to a pharmaceutical treatment regimen, and then to identify other characteristics that correlate with the sub grouping in outcomes. Examples include patient behavior, environmental variables, and gene variation. The goal is to enable academic research to identify characteristics that predict disease progression and complications so that standards of care can be further individualized and the knowledge base will be continuously enhanced.

One particularly interesting use of the research engine is specifically to correlate subgroups of patients based on treatment response and disease outcomes (phenotypic variables) to genetic variation. Many chronic diseases such as diabetes, hypertension, cardiovascular disease, obesity, and mental health disorders are thought to have a genetic component. The current effort uncovering single nucleotide polymorphism markers (SNPs), representing the common variations among the DNA of individuals, holds promise of understanding the genetic basis of chronic disease and related drug response (pharmacogenomics). The problem, however, remains that complex disease may have multiple etiologies, and the interaction of multiple genes with behavioral and environmental factors may underlie chronic disease occurrence and progression. This project will assess the feasibility of conducting genetic epidemiological research using longitudinal patient data on phenotype and environment variables collected through patient monitoring and management plan in a population of patients. The goal will be to: (1) develop a program that monitors phenotype and environmental variables for a specific set of diseases; (2) work with a clinical site to collect daily data from patients; (3) quantify phenotype and environment variability in sub-populations stratified by genetic factors; (4) develop linkages to life sciences projects capable of collecting and analyzing serum sample for genotyping; and (5) develop statistically appropriate design/analysis methods for assessing phenotype-genotype-environment associations.

Project Aims:
  I. Research and Development Phase (0-24$^{Th}$ Month)
    To develop a multi-dimensional model of disease and representative form of a patient's disease state; and to link the ongoing longitudinal monitoring to model, in terms of risk expression and aspects of care. Further, to structurally relate Knowledge Base and Information Base to the multi-dimensional model, which will enable the other objectives of the system.
    To create the required content including patient queries and dialogues, and to categorize it by key aspects of patient care, in order to ensure a holistic approach towards patient care.
    To develop a Dialogue Engine that will individualize medical management to the patient, and will allow the patient to be ubiquitously monitored, between clinical encounters, and in a manner that fits into his/her lifestyle. To link Dialogue Engine with Rendering Engine to ensure content presentation on an entire range of devices, and greater patient connectivity.
    To develop a Care Management Engine that automates content assignment on the basis of Information Base of a patient and Knowledge Base of the disease.
    To develop a Research Engine that permits researchers to identify subgroups and correlates of individuals with unique variables in their profile that set apart their condition from the rest of the individuals; and to test hypotheses on this database of individuals.
    To link remote care systems to Decision Support Tools, that will enable a paradigm shift from current manual processes and methods of risk stratification to automated individualized care; which will additionally optimize caregiver time, and enhance productivity.
    To develop an open interoperability standard for all components of the system, including Knowledge base, Information base, Decision Support Tools (DST) and Rendering Engine.
    To test the interoperability between Feedback Engine, Knowledge Base, Information Base, DST and Rendering Engine, and its compatibility other Integrated Project components, with currently used systems (including communication systems), and with external data systems, including legacy database systems.
  II. Validation Phase (25-48$^{th}$ month)
    To apply the system in the management of chronic health diseases in a demonstration project in multiple centers across Europe, in a randomized control study.
    To compare outcomes of disease managed by the system vis-a-vis that managed by present means, and aggregate data analysis for global impact. Outcomes analyses include health outcomes, cost-savings.
    To measure the impact the remote health management system has on certain key measures including: patient acceptability, satisfaction, utilization, clinical impact, medication compliance, quality of life, cost of care
    To conduct site specific data analysis by country, disease, and care model.
    To assess the feasibility of conducting genetic epidemiological research using longitudinal patient data on phenotype and environment variables collected through patient monitoring and management plan in a population of patients.

State of the Art:

Health Buddy and the iCare Desktop web service from Health Hero Network is a chronic care management solution that enables care providers to remotely monitor patients and detect problems early, while supporting daily patient education and treatment compliance. The Health Buddy appliance was introduced 1999 in the US and in 2003 in Europe. Over thirty care provider sites are currently monitoring 2,500 chronic patients everyday, and over two million patient surveys have been taken to date. Sites where the disease management solution has been implemented include Veterans Health Affairs, Mercy Health System and Kaiser Permanente in the United States. Implementation is in process at Universite Louis Pasteur (ULP), Strasbourg, France as a part of post-transplant care management program, and 150 patients are expected to be enrolled in the program in 2003. Additional implementations in process in Europe through agreements with Abbey Healthcare Ltd (Ireland) and Sananet B.V. (Netherlands).

Currently available programs include heart failure, coronary artery disease, diabetes, asthma, COPD, hypertension, and mental health, in addition to custom programs authored by care providers such as for post-transplant care and obesity.

The Technology:

The Health Hero platform consists of a series of web-based applications anchored by the Health Hero® iCare Desktop™ and a series of patient interfaces. The primary patient interface, the Health Hero Health Buddy®, is an easy-to-use information appliance placed in the patient's home. Health Hero provides other patient interfaces such as Health Buddy Web, for internet-savvy patients, and are in development stages for patient interfaces based on mobile technologies and interactive television. The web applications and patient interfaces combine to form a secure infrastructure that links providers to their at-home patients while supporting a flexible, cost effective means for daily monitoring.

FIG. 6.

I. Health Hero iCare Desktop

The Health Hero iCare Desktop application provides secure access to a series of web-based tools specifically designed for the patient management and workflow needs of a care provider. The iCare Desktop's capabilities include analysis of patient responses and alerts, review of patient trend data, and production of patient reports. The key feature of the iCare Desktop experience is that it enables care providers to quickly review the status of a large population of patients, which is also what differentiates it from other standard clinical information systems. The review process makes it possible to identify the patients in need of attention or follow-up based on a set of subjective and objective data points giving a total view of the patient's daily health status.

A care provider uses the iCare Desktop to view patient responses and identify responses within a patient population that are stratified as high, medium or low risk in the categories of symptoms, behaviors, and knowledge. This information is used to quickly assess which patients need an intervention on any given day. Care algorithms, Standard Operating Procedures (SOPs) and/or standing orders from the patient's physician guide the intervention. The Health Hero platform collects data that allows care providers to make clinical decisions based on longitudinal data, rather than a single telephone call or data point.

The efficiencies of the Health Hero Platform are realized through the improved data collection capabilities of the Health Buddy appliance and through the workflow features of the iCare Desktop. Disease management programs with care managers using the Health Hero Platform have more than double the number of patients previously managed using a manual approach to disease management.

Two specific features that greatly enhance workflow are the Inbox and the Patient Work List. These features provide two different views of patient results, allowing a care provider to deal with events as they happen using the Inbox, or in a more detailed manner with the Work List.

The Inbox feature of the iCare Desktop collects alerts, high risk and medium risk events in an interface similar to email software. As events are uploaded to the platform, the Inbox automatically creates a "to-do" list of critical tasks for each care provider's patient population. The items are classified by the standards of care and risk levels stipulated by the patient's care providers.

The care provider is presented with a category and a subject for each Inbox event, describing the results. A typical care provider workflow would consist of scanning the Inbox for results, and either clicking on the date to review the detailed results data, or using the check box to mark that the patient results were reviewed.

FIG. 5.

Whereas the Inbox collects a subset of patient results in a to-do list fashion, independent of the date and time, the Patient Work List is designed for review of a population in 24-hour time periods. This view provides the ability to quickly review the health of a population and determine which patients still require further assessment.

The Patient Work List provides options for how the patient results are reviewed. A care provider is able to adjust both the time period of results and the disease programs of patients to displayed. Supervisors and other iCare Desktop users with the correct permissions can also examine the Patient Work Lists of other care providers for quality control and "out of office" coverage.

A common question asked by those responsible for the management of a large population of chronically ill patients is, "How do I know I served all the patients who needed care under my SOPs?" The Patient Work List addresses this problem in real-time through the use of a graphical indicator to display the review status of each result. As shown in FIG. 6, each row of the Patient Work List includes a circular review indicator. A full circle indicates that the results have been reviewed by the care provider currently looking at the Work List. A half-filled circle indicates that another member of the care team reviewed the result. An empty circle indicates that the result has not been reviewed. This "at-a-glance" interface allows care providers to quickly confirm that an SOP has been followed when appropriate. Full audit logs of the review and disclosure of patient results, including the reviewer name, time and date of review, and method of review are logged and maintained by the Health Hero platform.

FIG. 6.

Care providers have access to patient data collected over time through the trend chart pages, which are graphical representations of the patient data. Analysis aids, such as baseline weights and target goals, can be displayed on the trend charts to provide guidelines for review.

FIG. 7.

Teams of care professionals provide the highest quality patient care and all members of the care team must be able to access clinical information for each patient in the manner that is the least disruptive to their existing workflow. The iCare Desktop provides robust reporting tools that facilitate the faxing, emailing, and printing of reports for review outside of the iCare Desktop workflow.

For those members of the care team who choose to use the web-based tools for patient management, the iCare Desktop is designed with role-based permissions, so each individual contributor to the patient's care is able only to interact with the specific patient data that is required to complete their professional function.

Providers access the iCare Desktop from a personal computer with an Internet connection. The iCare Desktop requires no installation of software or hardware, and little-to-no staff support from provider Information Technology (IT) groups. System maintenance, backup, and security is managed by Health Hero Network and it's networking partners.

II. Health Buddy® Appliance

Figure 8:
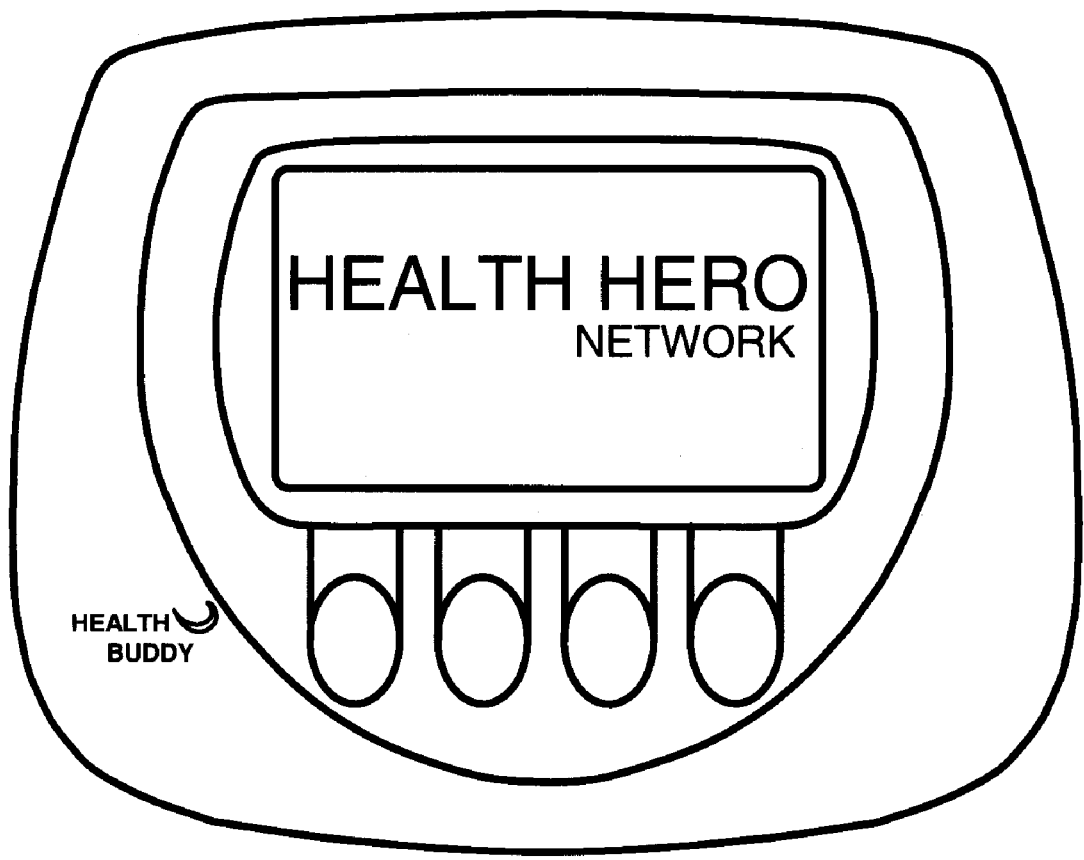
FIG. 8 is a diagram illustrating the Healthy Buddy device in accordance to an exemplary embodiment of the present invention.
Figure 9:
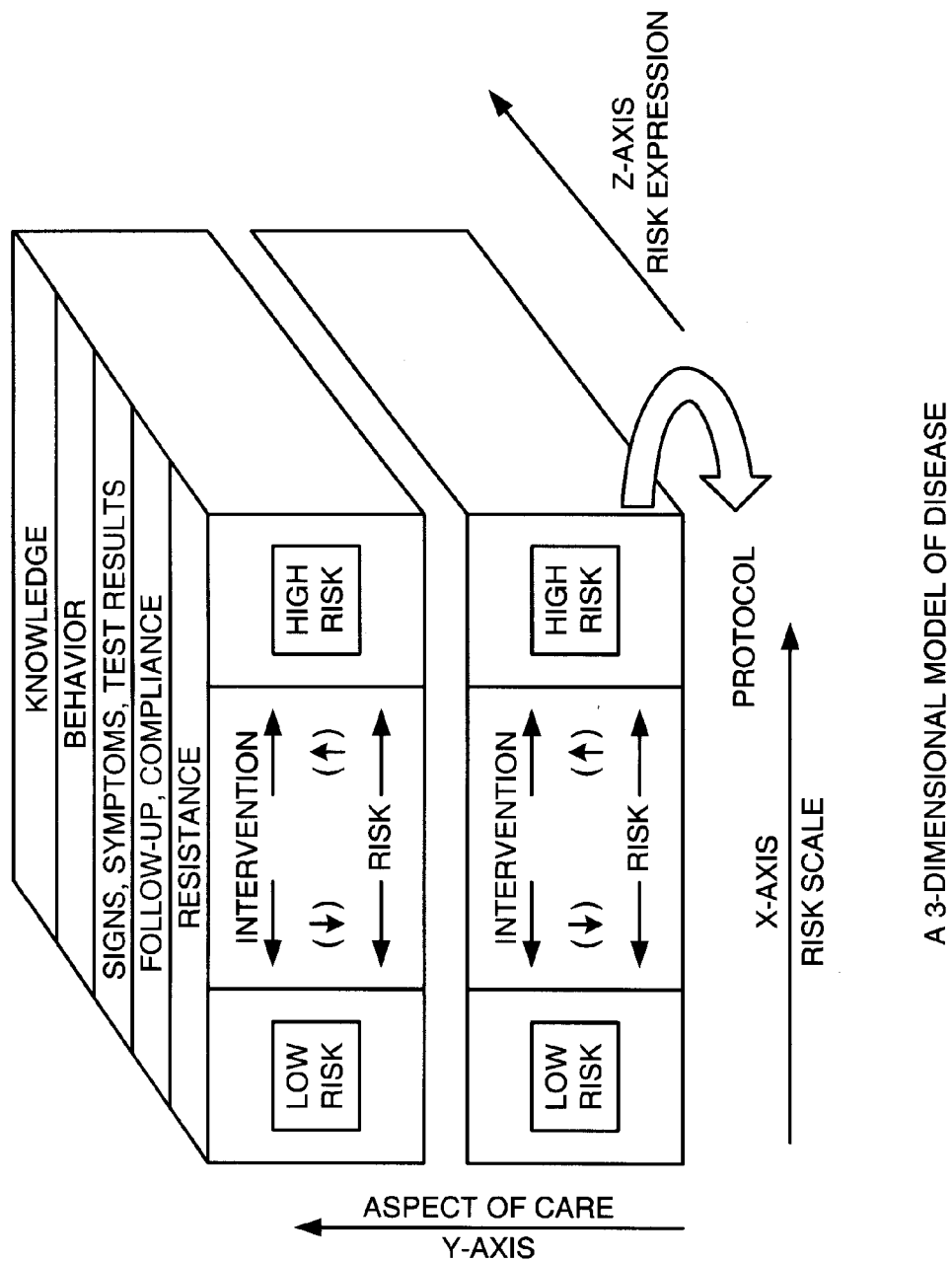
FIG. 9 is a diagrammatic representation of a 3-Dimensional Model of Disease in an exemplary embodiment of the present invention.
Figure 10:
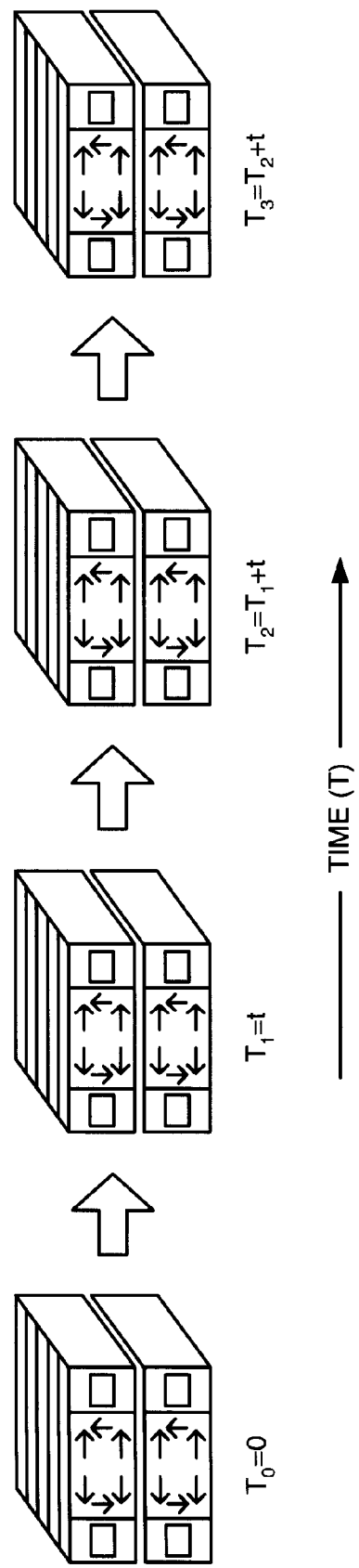
FIG. 10 is a diagrammatic representation of a 4-Dimensional Model of Disease in an exemplary embodiment of the present invention.
Figure 11:
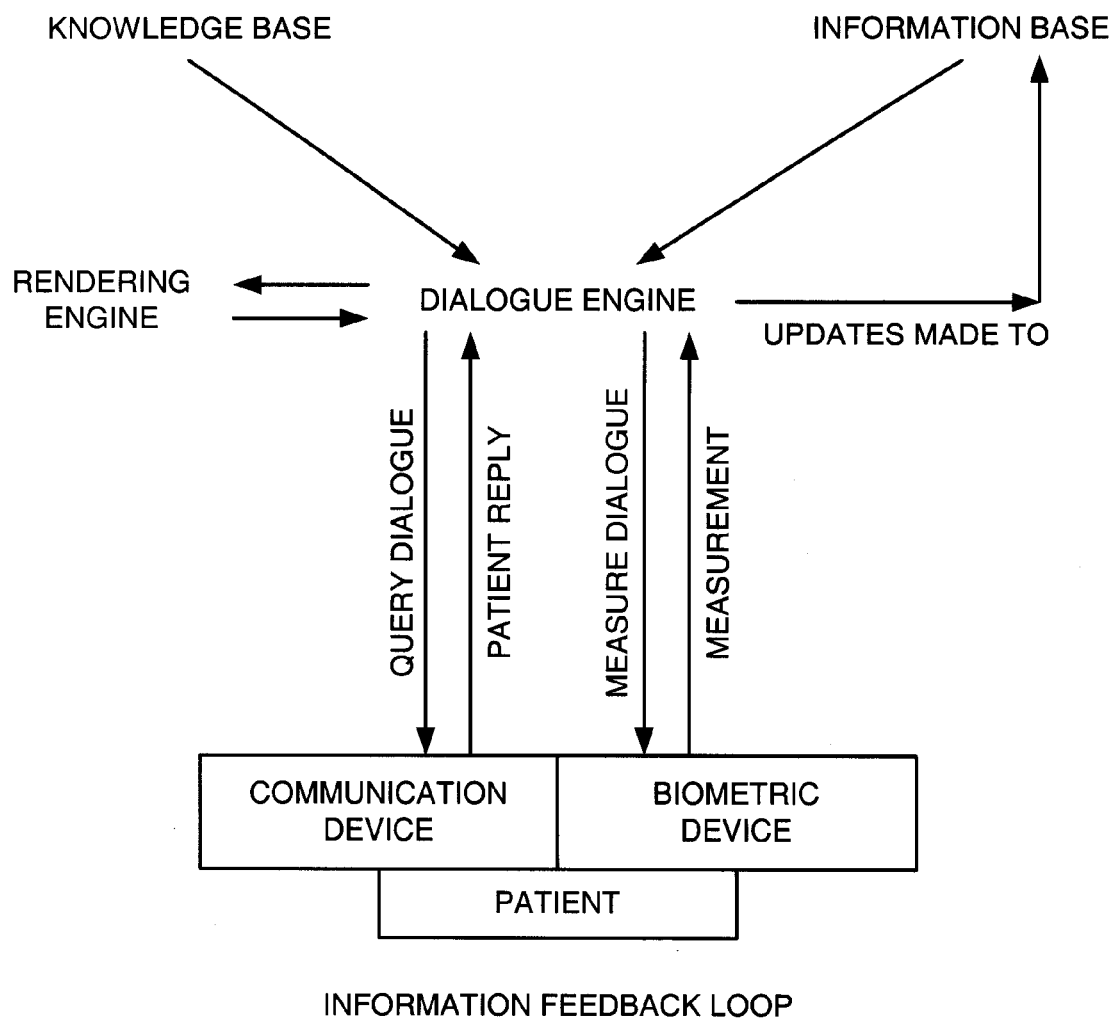
FIG. 11 is a diagram illustrating an Information Feedback Loop in accordance to an exemplary embodiment of the present invention.
Figure 12:
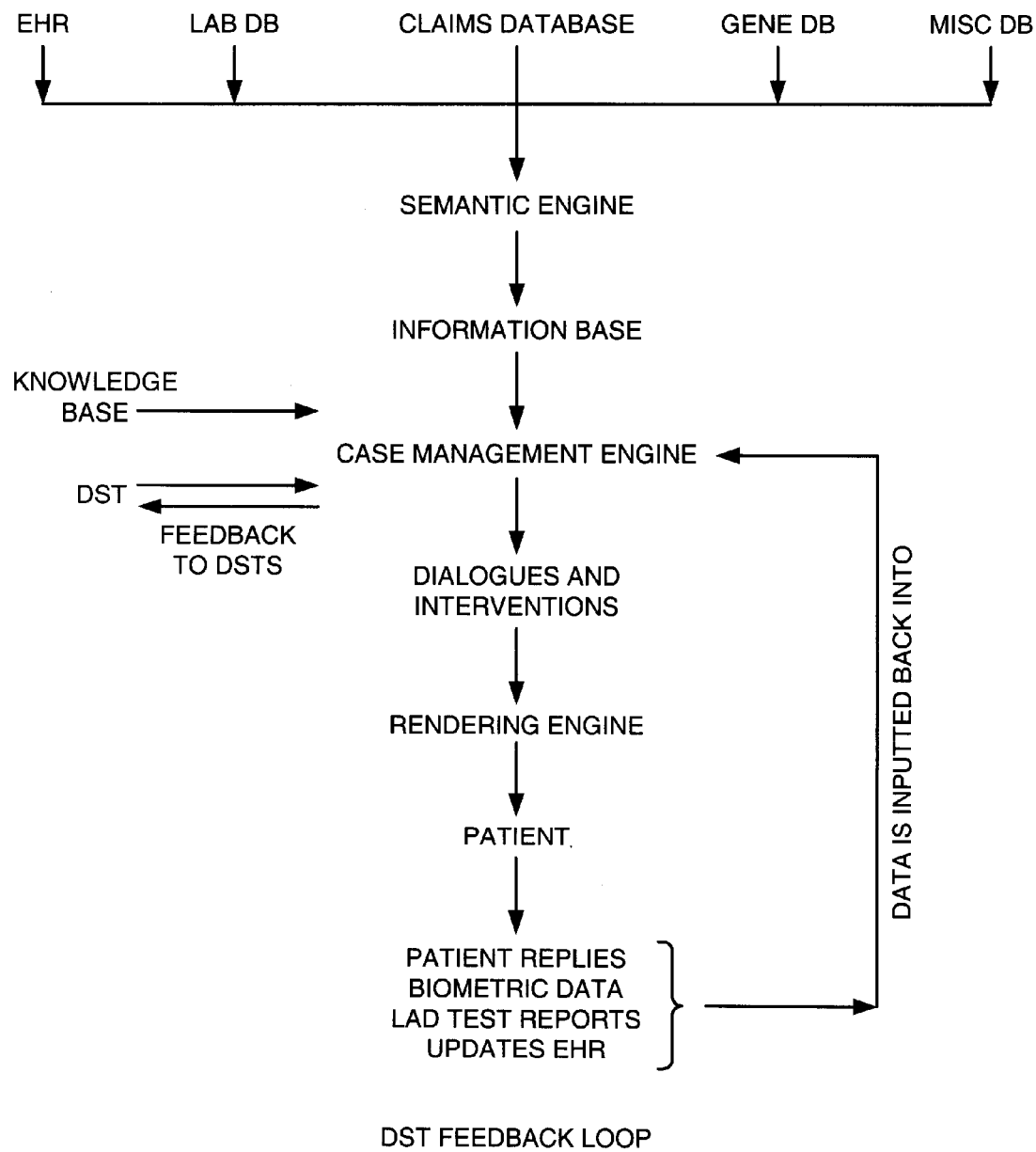
FIG. 12 is a diagram illustrating an DST Feedback Loop in accordance to an exemplary embodiment of the present invention.
Figure 13:
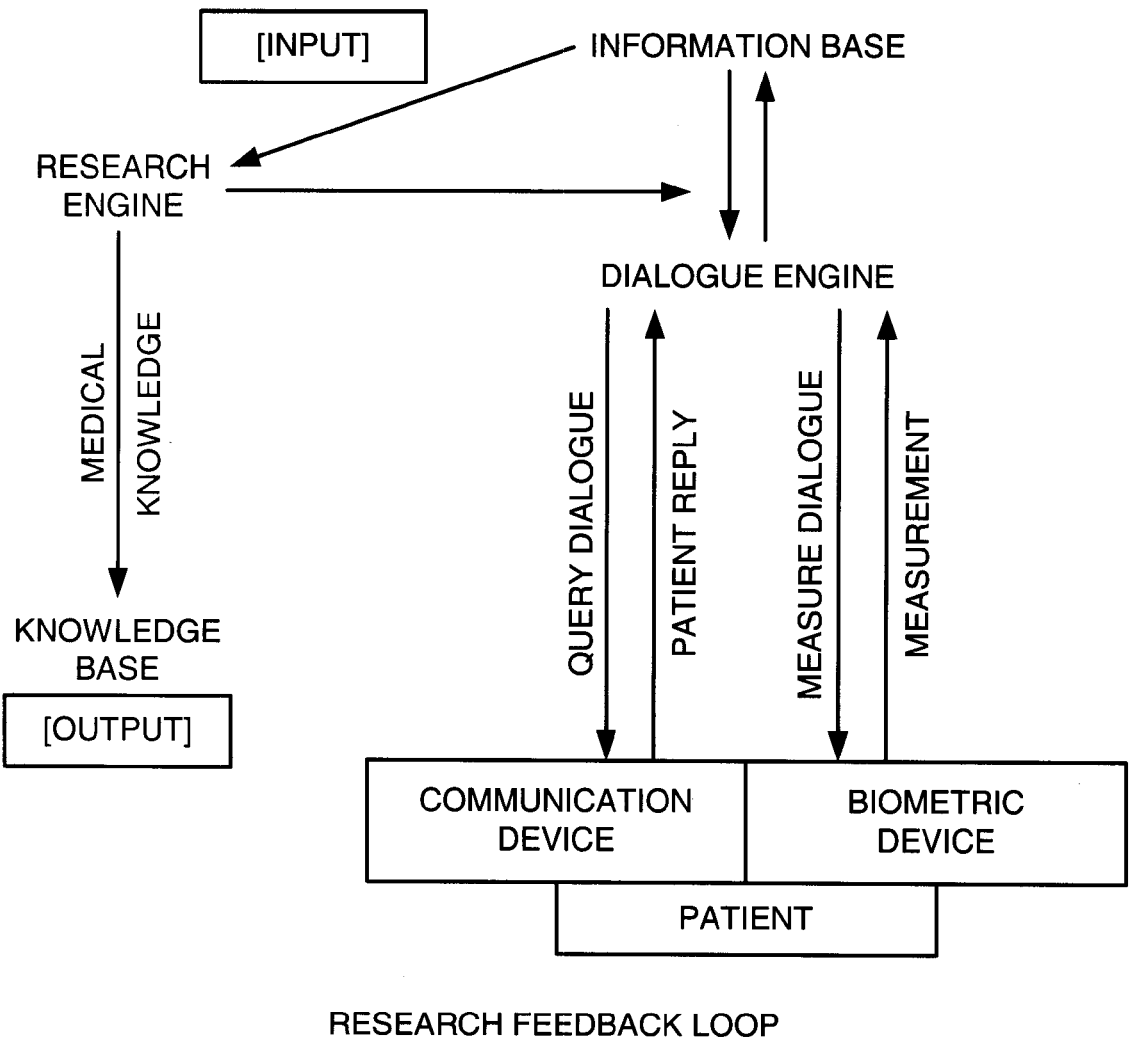
FIG. 13 is a diagram illustrating an Research Feedback Loop in accordance to an exemplary embodiment of the present invention.
Figure 19:
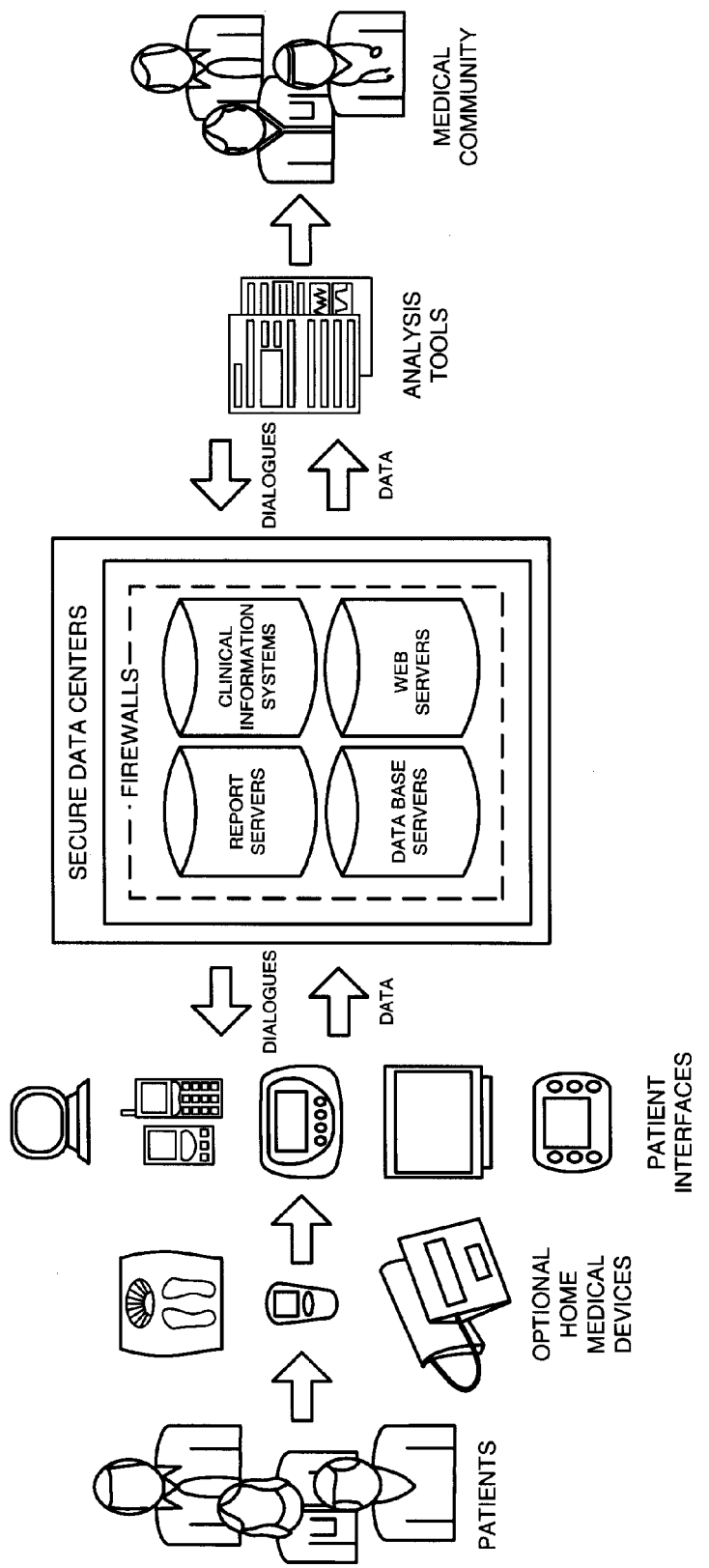
Figure 20:
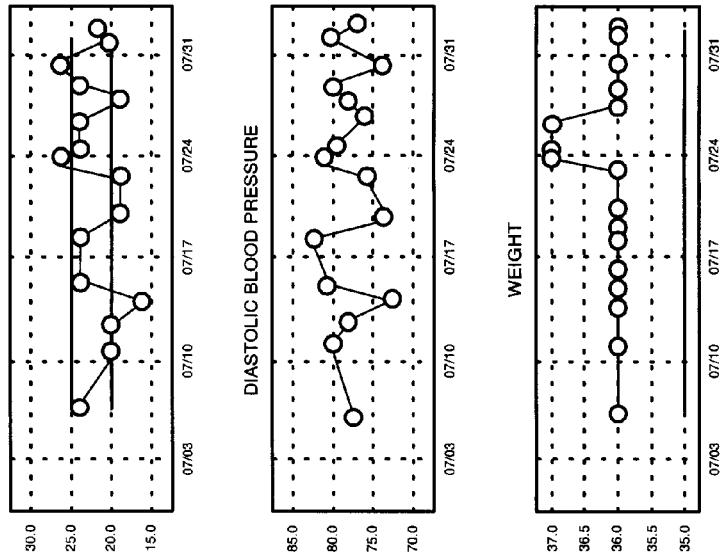
Figure 25:
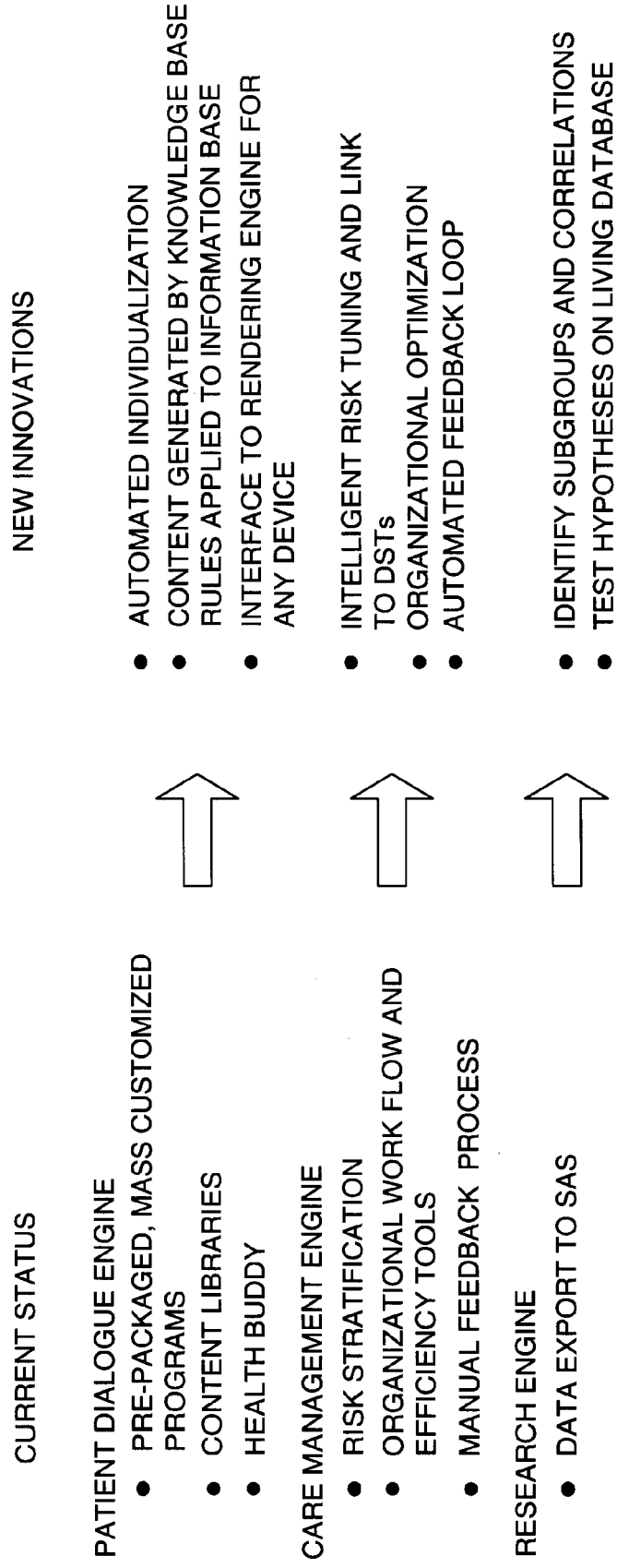
Figure 26:
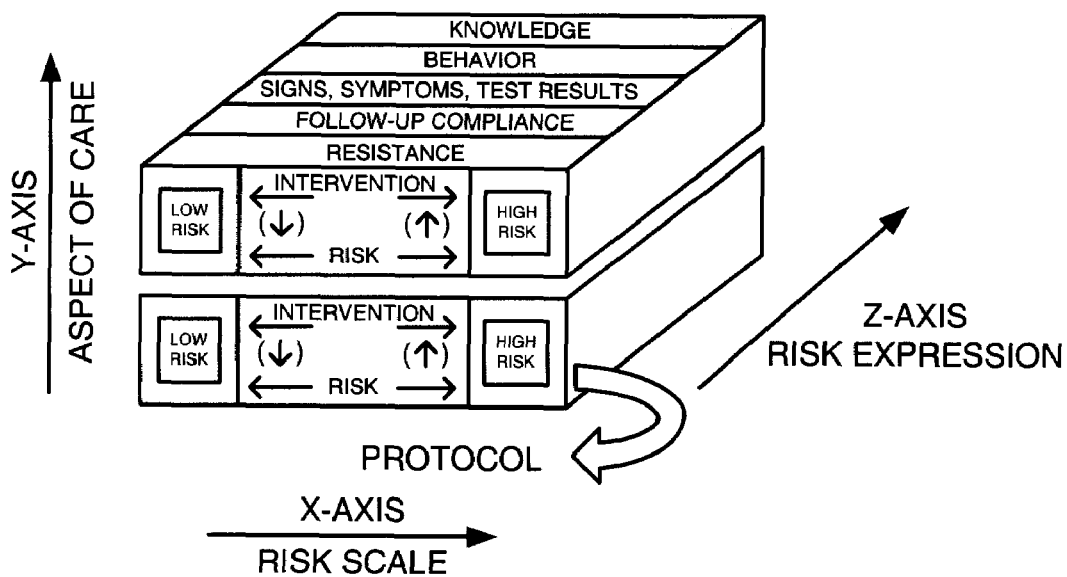
Figure 27:
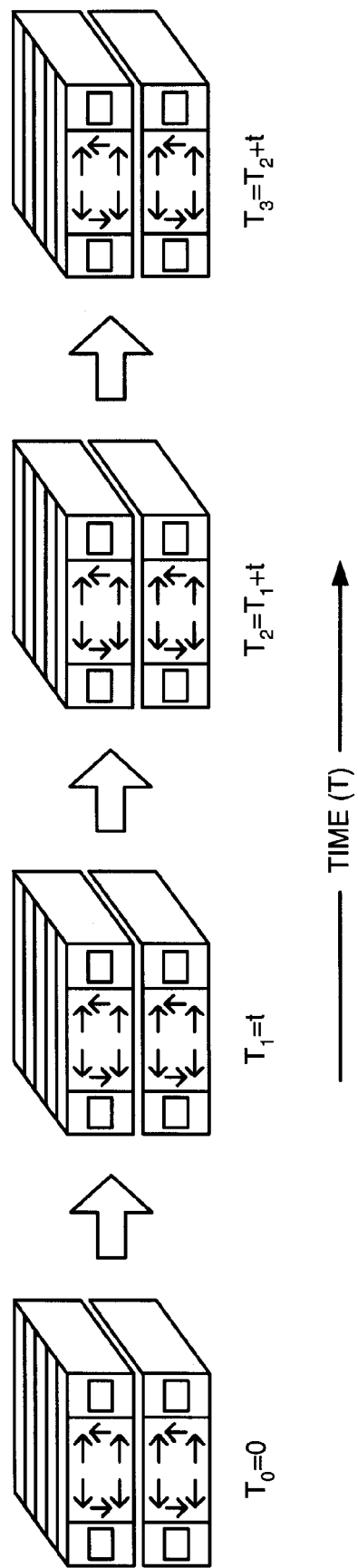

The Health Buddy appliance, shown in FIG. 8, serves as the primary patient interface for secure communication between patients and the network. The Health Buddy was designed as an easy-to-use communication appliance for placement in the patient's home, and has gone through significant commercial validation as a welcome in-home healthcare tool.

The ease of use begins with the Health Buddy installation process, which is most often conducted by the patient with no assistance. The Health Buddy requires a standard telephone outlet and standard power outlet, and requires no additional telephone lines, software, or computer experience. When power is applied, the Health Buddy presents the patient with an interactive Health Buddy tutorial, and then within one hour of taking the tutorial, the patient receives their first Health Buddy survey.

The Health Buddy provides the patient with at least one survey per day. The surveys are designed to enable patients to easily respond to a range of questions, that relate to important aspects of care for their specific condition. Once the patient answers the questions in the survey, the Health Buddy stores and transmits the information back to the care providers, who will review the data using the iCare Desktop. Although the standard model of care for patients uses a once-per-day survey transmission mode, the transmission of results can be customized to upload patient data at any desired frequency, including in response to a particular patient result.

FIG. 8.

The Health Buddy is intended to gather quantitative and qualitative patient information through a simple question, answer and education session. In some cases, it is important to augment quantitative and self-reported qualitative data with information collected directly from medical devices. The Health Buddy appliance, through the Buddylink™ feature, allows the collection of data from medical devices, such as blood glucose meters, weight scales, and blood pressure cuffs. The objective data is collected during the survey process so that the patient still benefits from the education, behavior modification, and personalized responses.

The benefits of employing the Health Buddy and the iCare Desktop web service in disease management have been validated in articles published in several peer-reviewed journals. Briefly, the Health Hero Disease Management Programs have shown clear benefits over other programs, in terms of—

Cost Benefits: Health Buddy reduces hospital admissions and costs by detecting problems before they become a crisis. A recent study at the Veterans Health Affairs reported a 60% reduction in hospital bed days of care in a one year trial with 791 CHF, COPD, diabetes, and hypertension patients in a chronic care program in which most patients were monitored daily using Health Buddy. Similar cost savings were reported in Medicare HMO patients. (Meyer et al, Disease Management 2002; 5: 87-94. Vacarro et al, Disease Management 2001; 4(3): 1-10.)

Access to Care: Health Buddy increases access to care by expanding the capacity of care providers to monitor patients using existing resources. Through daily communication, patients are able to access timely care before conditions become a crisis. At Mercy Health System, a part-time nurse provides daily monitoring for 425 heart failure, diabetes, and hypertension patients. With telephone-based monitoring only, a full-time nurse could provide weekly monitoring to less than 100 patients. The efficiency achieved through Health Buddy allowed for coverage of uninsured patients who otherwise would have received no care at all. (Cherry et al, Diabetes Technology & Therapeutics; 4(6): 793-791.)

Quality of Care: Health Buddy improves quality of care by providing timely, relevant, and actionable information to healthcare providers so that care can be coordinated in a quality assured process. Care providers are able to detect complications before they become acute and result in hospital admissions, providing quality care that reduces painful and costly complications by maintaining patients in a healthier state. Health Buddy also improves patient outcomes by improving treatment compliance through educating, motivating and monitoring patients daily. (Cherry et al, Lippincott's Case Management 2000: 5(5): 191-198. Guendelrnan et al, Archives of Pediatric and Adolescent Medicine 2002: 156: 114-120.)

Scope for Innovation:

TABLE

The contribution of Feedback Engine in terms of innovation

| | State of the Art | Scope of Innovation |
|---|---|---|
| Patient Dialogue Engine | Pre-packaged, mass customized programs | Automated individualization of programs |
| | Content Libraries | Content Generated by knowledge base rules applied to information base |
| | Health Buddy | Interface to Rendering Engine for any device |
| Care Management Engine | Risk Stratification | Intelligent risk tuning and link to DST |
| | Organized workflow and efficiency tools | Organizational optimization |
| | Manual feedback process | Automated feedback loop |
| Research Engine | Data Export to SAS | Identify subgroups and correlations Test hypotheses on living database |

Multi-Dimensional Model of Disease:

I. The 3-Dimensional Model of Disease

FIG. 9.

The above diagram illustrates a three dimensional model of disease. In this model, a patient's health at a point in time is determined on a relative risk scale. The Y-axis contains slabs, each relating to a specific aspect of care. For instance, in a multi-system disease like Diabetes, one slab relates to blood glucose control, another to the cardiovascular system, still others to foot care, the neurological, renal and ophthalmic systems. Given the complex multiple interactions between different aspects of care, there may be occasional overlap between different slabs. For instance, glucose control, when applied in the long-term sense, is related to the cardiovascular, renal and most other systems. In such cases, each factor of interest is represented separately and independently on the Y-axis.

Each aspect of care in the individual patient is further modulated by a patient's knowledge of disease (in that aspect of care), patient behavior, signs, symptoms, test results, and general resistance to medical advice. Each such aspect of risk expression is represented in the model on the Z-axis. A specific aspect of care (Y) for a specific expression of risk (2) is termed a 'health context'. The X-axis relates to the relative level of risk exhibited by an individual patient for each health context. Lower x values of a patient indicate a better state of health.

For example, in case of blood glucose control in diabetes, the actual behavior of the patient, and disease outcomes are a function of the 1. Patient's knowledge—a patient with a greater knowledge (lower risk) of the long-term complications of diabetes, and its relationship to blood glucose control is more likely to be compliant with the diabetic diet and regimen (better outcome).

2. Behavior—Humans exhibit varying behaviors regardless of the level of knowledge of their disease condition. Some individuals are more health conscious (lower risk) than the others.

3. Signs, Symptoms, and test results—. A patient whose blood glucose values are consistently within the normal range (lower risk) gets the requisite positive feedback, encouragement, and impetus to further adhere to the prescribed medical regimen. Conversely, patients who develops complications of medication, such as nausea, vomiting or hypoglycemic attacks are at a greater risk of being non-compliant with medical advise.

4. Follow-up, compliance, and Resistance-On continued follow-up, one or more of the above factors may change. For instance, as a patient's knowledge of his/her disease condition increases, he/she may be more inclined to be compliant with the medical regimen. Resistance is defined as the tendency of patients to resist medical care and the changes it entails with regard to one's lifestyle and habits. In the context of the disease model, resistance is additionally related to a patient's perception of the value of medical regimens.

The Fourth Dimension: Time—The three dimensional model is 'static', in that it doesn't describe the changes that take place in the patient's disease state with time, nor is it descriptive about the effects of various interventions and medical therapies on the Information Base. To this end, the fourth dimension of time is added to the three-dimensional model. The aim of disease management is to achieve the lowest overall risk in a group of patients.

FIG. 10.

It permits outcomes analysis to be performed. Additionally, it allows one to study (and test) effects of multiple expressions of risk and aspects of care with regard to one another, as a function of time, in a single patient.

II. Description of System Components in Relation to the Multi-Dimensional Model.

Knowledge sources and medical literature typically supply recommendations as to 'standard of care' in the form of care management algorithms. However, these algorithms would need to be interpreted and applied into the system by Decision Support Tools and Care Management Engine. Further, the format and logic would need to be common for all the system sub-components, in order that interfacing is made possible by the use of Application Program Interfaces. Finally, the logic has to be mapped to the multi-dimensional model of disease. The proposed system architecture, type, nature, and format of data exchange between the system's components will be better understood when explained in reference to standard care management algorithms. One such algorithm, specifically an algorithm relating to the management of patients with congestive heart failure by Care Managers is given in the table below—

TABLE

A health context management algorithm

| | |
|---|---|
| TITLE: | CONGESTIVE HEART FAILURE SURVEILLANCE DURING DIURETIC ALGORITHM |
| POLICY | 1. Function:<br>To outline the nursing management of patients who are referred by their physician to Health Buddy Congestive Heart Failure Program. Registered nurses independently titrate the patient's regularly prescribed diuretics and potassium based on the patients symptoms and weight gain using an approved algorithm.<br>Circumstances under which the RN may perform this function:<br>Registered nurses who work in Health Buddy Congestive Heart Failure Disease Management Program may initiate this standardized procedure when directed by the patients physician.<br>Patient contraindications to use of this standardized procedure include pulmonary edema, new or refractory chest pain, new or sustained arrhythmia, syncope. |
| PROTOCOL | 1. Definition - The Health Buddy Congestive Heart Failure Disease Management Program is an outpatient-based approach to managing chronic CHF patients, where Registered Nurses provide education, support, and clinical follow-up to patients with congestive heart failure under the direction of a Physician.<br>2. Assessment - Assess patient for signs and symptoms of worsening congestive heart failure<br>Breathlessness, paroxysmal nocturnal dyspnea, orthopnea, dyspnea at rest<br>Weight gain<br>Edema<br>Compliance with medication regime<br>Compliance with dietary restriction |

| PROCEDURAL STEPS | KEY POINTS |
|---|---|
| 1. Once a change in status has been indicated, interview patient via telephone to verify the patients status.<br>2. Interview patient to determine subjective complaints of SOB, fatigue and other signs & symptoms of CHF.<br>3. Based on the patients subjective symptoms and current weight, implement the following. | Total daily doses of diuretics should not exceed the following limits unless approved by physician: Lasix 240 mg, Bumex 10 mg, Metolazone 5 mg, Demadex 240 mg. |

| Patient's Symptoms | Weight Gain in Pounds | Treatment Category | Treatment Legend |
|---|---|---|---|
| No new symptoms | 1-2 | Restrict Salt | 1 = Extra dose of the patients regularly prescribed diuretic |
| | 3-4 | 1 | and potassium now*. |
| | >4 | 2 | 2 = Extra dose of the patient's regularly prescribed diuretic |
| New or worsening paroxysmal nocturnal dyspnea | 1-2 | 1 | and potassium now, then an extra daily dose for 3 days*. Daily phone calls from Health Buddy nurse. Obtain renal panel within 48 hours if current creatinine >1.8. |
| | 3-4 | 3 | 3 = Double dose of the patient's regularly prescribed |
| | >4 | 3 | diuretic and potassium now, then an extra daily dose for 3 |
| Orthopnea | 1-2 | 2 | days*. Health Buddy nurse will notify patient's primary |
| | 3-4 | 3 | physician. Obtain renal panel within 48 hours if |
| | >4 | 3 | current creatinine >1.8. |
| Shortness of breath when seated | 1-2 | 2 | 4 = Double dose of the patient's regularly prescribed diuretic and potassium now and again in 4 hours*. Health |
| | 3-4 | 3 | Buddy nurse will notify patient's primary physician; office |
| | >4 | 4 | visit scheduled. Obtain renal panel (if current creatinine >1.8) and Mg++ within 48 hours. |
| Pulmonary edema refractory to treatment category 4, chest pain (new or refractory to nitro), arrhythmia (new or sustained), syncope | | 5 | 5 = Refer to emergency department. Health Buddy nurse will notify physician and appropriate emergency department |

TABLE-continued

A health context management algorithm

| | | |
|---|---|---|
| 4. | To manage the patient who loses weight below their pre-determined dry weight: 2-3 pound weight loss - halve diuretic for one day; if recurrent, reduce to half dose every other day.* 4-6 pound weight loss - reduce diuretic to half dose daily, obtain renal pane*, and notify physician. 7 or more pounds - hold diuretics, obtain renal panel*, and notify physician. | *Essential to reduce potassium supplements an equivalent amount. |
| 5. | To manage the patient with excessively rapid weight loss: 3-5 pounds in 24 hours** -- confirm appropriate potassium replacement Weight loss of more than 5 pounds in 24 hours** -- confirm appropriate potassium replacement, obtain renal panel, and notify physician. | **If weight loss continues longer than 24 hours, obtain renal panel and notify physician. |
| 7. | Follow-up phone calls from Health Buddy nurses are required for treatment categories 2, 3, 4, and 5 and for all patients with weight loss below dry weight and excessively rapid weight loss within 72 hours of initiating the treatment change. | The primary physician must be consulted if the patient meets criteria for emergency department referral, weight loss below dry weight of 4 or more pounds, and excessively rapid weight loss of more than 5 pounds in 24 hours. |

Knowledge Base: Knowledge Base, the summation of medical knowledge and concepts is organized by location pointers, expressions that define the location of any aspect of disease on the multi-dimensional model, and protocols, which are logical expressions that define the relationships between the health contexts, and the actions that need to be taken for possible combination of factors within the health context. Within the multi-dimensional model of disease, location pointers are represented on the X, Y- and Z-axis.

Every possible piece of information that is collected by the system is mapped on to the 3-dimensional model.

In the above example,

| | | | | |
|---|---|---|---|---|
| DIRECTIONAL POINTER: | CHF SURVEILLANCE | | | |
| DISEASE: | CONGESTIVE HEART FAILURE | | | |
| ASPECT OF CARE: | DIURETIC MANAGEMENT | | | |
| KNOWLEDGE: | OF ORTHOPNEA | YES | NO | |
| | OF PAROXYSMAL NOCTURNAL DYSPNEA | YES | NO | |
| | OF NECESSITY TO RESTRICT SALT | YES | NO | OCCASIONALLY |
| BEHAVIOR: | EXERCISING REGULARLY | YES | NO | OCCASIONALLY |
| | RESPONDS TO HEALTH BUDDY | YES | NO | OCCASIONALLY |
| | RESPONDS TO PHONE CALLS | YES | NO | OCCASIONALLY |
| SIGNS: | | | | |
| SYMPTOMS: | | NO NEW SYMPTOMS | NEW OR WORSENING PND | ORTHOPNEA |
| TEST RESULTS: | WEIGHT GAIN | 1-2 LB | 3-4 LB | >4 LB |
| | CREATININE | <VALUE> | | |
| | WEIGHT | <VALUE> | | |
| | K+ LEVEL | <VALUE> | | |
| COMPLIANCE: | COMPLIANCE WITH MEDICATION | GOOD | MODERATE | POOR |
| | COMPLIANCE WITH DIET | GOOD | MODERATE | POOR |
| FOLLOW UP: | | | | |

Thus, Knowledge Base defines the location of the particular attribute on the model. It is common to all patients with a single disease. Further, the 'risk-states' that are given to a particular variable is defined at the time of creation of the model. For example, in the health context of Behavior (Responds to phone calls), a value of 'Yes' will lie towards the low risk end of the X-axis, while, a value of 'No' will lie towards the high risk end. For continuous variables, for example, the results of a laboratory test, or Creatinine values, the value of a health context is represented as such, on a scale. In case where a low value is medically significant, such as a low serum potassium value, it is represented by two contexts, one for hypokalemia (low potassium) and another for hyperkalemia (high potassium values). On the contrary, if low values of a measurement have no medical significance, for example Creatinine value, then it is represented by a single context.

In order to automate patient care, and to achieve the other objectives of the system, it is necessary to incorporate into the system, the logic that will enable it to decide on a course of action to be taken, or a treatment plan, which are the Protocols. Protocols tell the system the action that needs to be taken for any of a combination of unique variables in the Information Base. Protocols are the 'threads' or connections that link the discrete data components that ultimately forms the Information Base.

In the above context,

| PROTOCOL: DIURETIC PRESCRIPTION |
| --- |
| IF SYMPTOMS = 'NO NEW SYMPTOMS' AND WEIGHT GAIN = '1-2' |

| PROTOCOL: DIURETIC PRESCRIPTION |
| --- |
| THEN ACTION: RESTRICT SALT |
| IF SYMPTOMS = 'NO NEW SYMPTOMS' |
| AND WEIGHT GAIN = '3-4' |
| THEN ACTION 1.: INCREASE_DOSE_DIURETIC |
| THEN ACTION 2: GIVE PATIENT POTASSIUM |
| IF SYMPTOMS = 'NO NEW SYMPTOMS' |
| AND WEIGHT GAIN = '>4' |
| THEN ACTION 1.: INCREASE_DOSE_DIURETIC |
| THEN ACTION 2: GIVE PATIENT POTASSIUM FOR 3 DAYS |
| THEN ACTION 3: ALERT CARE MANAGER: TO PHONE PATIENT |
| THEN ACTION 4: OBTAIN RENAL PANEL |

Information Base—This is individual to a patient, and is created in response to the data (responses to queries), measurements of the patient, and external data sources. In the 3 dimensional model of disease, a new 3-dimensional model is created for each new piece of information. In general, the information base provides a health profile of the individual at that point of time, and is sufficient for deciding the care management, when used in reference to Knowledge Base. The table below depicts the Information Base of a particular patient at a point in time.

| | | | | |
| --- | --- | --- | --- | --- |
| PATIENT NAME: | SCOTT, JANE | | | |
| DISEASE: | CONGESTIVE HEART FAILURE | | | |
| DATE, TIME | APR. 9, 2003, 1400 HRS, GMT | | | |
| KNOWLEDGE: | OF ORTHOPNEA | | | |
| | OF PAROXYSMAL DOCTURNAL DYSPNEA | YES | | |
| | OF NECESSITY TO RESTRICT SALT | YES | | |
| BEHAVIOR: | EXERCISING REGULARLY | | | OCCASIONALLY |
| | RESPONDS TO HEALTH BUDDY | YES | | |
| | RESPONDS TO PHONE CALLS | | | OCCASIONALLY |
| SYMPTOMS: | | NO NEW SYMPTOMS | NOW OR WORSENING PND | ORTHOPNEA |
| TEST RESULTS: | WEIGHT GAIN | | 3-4 LB | |
| | CREATINE | 1.7 | | |
| | WEIGHT | 149 LB | | |
| | K+ LEVEL | 4.4 | | |
| COMPLIANCE: | COMPLIANCE WITH MEDICATION | GOOD | | |
| | COMPLIANCE WITH DIET | | MODERATE | |

However, in some cases, current Information Base alone is insufficient in deciding the course of management of the patient. Previous or baseline values are required for comparison. This is especially the case where the laboratory values are used. For example, in this patient with Congestive Heart Failure, a weight of 65 kg, has no meaning in itself, unless it is compared with the patient's previous weight. A weight gain could be the first sign of fluid accumulation and impending heart failure.

Serial follow-up of Information Base has immense Research utility, for example in outcomes analysis, and in con-elating the effects of a new drug or intervention on an entire range of patient variables.

Decision Support Tools—Decision Support Tools determine the extent to which provided care is consistent with the consensus standard of care. For example, in Diabetes, knowledge base protocols will require that the patient has a HbA1c test every three months. The following protocol logical expression is applied to determine if the standard of care has been followed.

| PROTOCOL |
| --- |
| IF [DATE (TODAY)] - [DATE (HBA1C-TEST)]≧90, THEN DOACTION: INFORM CARE_MANAGER (PATIENT) |

The following protocol 'tells' the Decision Support Tools the effects that a particular intervention has on the risk factor levels of different health contexts. On increasing the daily injected insulin dose, the risk of developing hypoglycemic episodes is raised significantly, also there is a risk of weight gain and an increased cost of medication to the provider. Finally, the biometric device is scheduled to receive three blood glucose samples for a week.

```
if INTERVENTION (INCREASE_INSULIN_DOSE) = 'TRUE'
THEN RISK (HYPOGLYCEMIC_EPISODE) = RISK + (VAR1)
ALSOTHEN RISK (WEIGHT_GAIN_NEAR_TERM) = RISK +
(VAR2)
ALSOTHEN (MEDICATION_COST) = (MEDICATION_COST) +
(VAR3)
ALSOTHEN DO (TEST_GLUCOSE_VALUE) = 3TIMES/DAY * 1
WEEK
```

In deciding the course of management of the patient's condition, DSTs reference the Information Base and the Knowledge Base.

Feedback Loops:

The Feedback Engine will enable a regular and ongoing interaction between the patient and the care manager, physician and researcher, outside of the clinical encounter. There will be three main types of feedback loops—the Information Feedback Loop, the DST Feedback Loop, and the Research Feedback Loop.

The Information Feedback Loop—The Information Feedback Loop provides feedback to the Information Base. It is the feedback loop from the perspective of a patient, enabling individualized communication, and ubiquitous monitoring of a patient. Updates to the patient Information Base are made automatically, and in real time, thus allowing for reduced latency from the provision of information to action taken. Dialogues are not only customized to comprehensive and updated information, but also are rendered for output in a variety of formats.

FIG. 11.

In the first step, Dialogue Engine links to Knowledge Base and Information Base in order to create and select dialogues that are most suited to the patient's Knowledge Base and Information Base. In the next step, Dialogue Engine interfaces with Rendering Engine to format the dialogues for transmission and uptake by the patient communication device and biometric device. Query dialogues are sent to the Communication Device, for display to the patient. Additionally, Dialogues are sent to the Biometric Device, either directly, or via communication device with commands to collect measurements of physiological variables. Replies of the patient and measurements from biometric devices are re-routed to the Dialogue Engine through the same communication system. The Dialogue Engine further interfaces with Rendering Engine, in order to interpret the signals, and appends the newly collected data to the Information Base. The updated Information Base is in turn used in subsequent iterations of the patient management process.

DST Feedback Loop—The DST Feedback Loop provides feedback to Decision Support Tools, and it's updating in real time, resulting in care that is provided on the basis of patient data that is updated in real time.

FIG. 12

In the first step, the Care Management Engine interfaces with Information Base, Knowledge Base, and DSTs to create Dialogues and Interventions suited to the Patient's disease condition. These dialogues and interventions are rendered to the format of the communication by rendering engine. Patient replies to query dialogues, Biometric test results, and updates of Laboratory and EHRs are fed back into the Information Base. The feedback provided from the received data is used to create better decision Support Tools that enable better automated processing of patient care.

Research Feedback Loop

FIG. 13.

Research Feedback Loop is primarily used by a researcher to make new discoveries and to test hypotheses on the system. Information Base is organized in the form of a neural network, thus enabling the Research Engine to scan the data, and to look for the correlates in the data, or events that have a greater correlation than can be explained by chance alone. These correlates are forwarded to the Researcher, who will form a hypothesis. In order to test the hypothesis, the Researcher may use Research Engine to interface with Dialogue Engine, and use it to create Dialogues and requests for measurements from Biometric Device. The results of the queries and tests measurements are forwarded to Information Base, and thence to the Research. Further statistical analyses may be performed, and associations may be elicited. For example, the Researcher may be able to prove the existence of an unknown factor in a chronic disease that causes different people to respond differently to medication. Further correlation with molecular and genetic studies may be done to prove or refute the hypothesis.

What is claimed is:

1. A system comprising:
   a first server storing (i) knowledge data in a knowledge base and (ii) information data in an information base, wherein an ontology specifies how said knowledge data applies to one or more specific disease conditions and a patient population; and a second server configured to communicate with one or more selected devices of a plurality of patient devices via a network, said second server including (i) a rendering engine configured to (a) generate one or more queries in response to both said knowledge data and said information data and (b) transmit said queries to said selected devices and (ii) a feedback engine configured to (a) receive one or more responses from said selected devices, (b) generate feedback data by processing said responses and (c) to update said information base with said feedback data, wherein said knowledge base comprises (i) a plurality of multi-dimensional models corresponding to a plurality of diseases and (ii) a plurality of location pointers that define a plurality of locations of a plurality of aspects of said diseases in said multi-dimensional models.

2. The system according to claim 1, wherein said feedback engine comprises a dialog engine configured to customize said queries based on one or more biometric devices used by said selected devices to collect physical measurements from one or more selected patients of said patient population.

3. The system according to claim 2, wherein said feedback engine comprises a care management engine configured to generate gap data by comparing a standard care with a delivered care provided to said selected patients.

4. The system according to claim 3, wherein said second server comprises one or more decision support tools configured to generate one or more reports that present said gap data in a human readable format.

5. The system according to claim 1, wherein said feedback engine comprises a research engine configured to query said information base to identify a subgroup of said patient population having a particular characteristic associated with at least one of said specific disease conditions.

6. The system according to claim 5, wherein said research engine updates said knowledge data in said knowledge base in response to a result of said query.

7. The system according to claim 1, further comprising a third server in communication with said first server and executing an application program configured to generate a web page containing a status of at least eight of said patients.

8. The system according to claim 7, wherein said status comprises a plurality of risk levels in each of a symptom category, a behavior category and a knowledge category.

9. The system according to claim 1, further comprising a semantics engine configured to integrate external data received from one or more sources external to said system into said information base.

10. A method for processing medical knowledge, comprising the steps of:
(A) storing both (i) knowledge data in a knowledge base and (ii) information data in an information base in a first server, wherein an ontology specifies how said knowledge data applies to one or more specific disease conditions and a patient population;
(B) generating one or more queries in response to both said knowledge data and said information data in a rendering engine of a second server;
(C) transmitting said queries via a network to one or more selected devices of a plurality of patient devices;
(D) receiving one or more responses via said network from each of said selected devices;
(E) generating feedback data by processing said responses in a feedback engine of said second server; and
(F) updating said information base with said feedback data, wherein said knowledge base comprises (i) a plurality of multi-dimensional models corresponding to a plurality of diseases and (ii) a plurality of location pointers that define a plurality of locations of a plurality of aspects of said diseases in said multi-dimensional models.

11. The method according to claim 10, further comprising the step of:
customizing said queries based on one or more biometric devices used by said selected devices to collect physical measurements from one or more selected patients of said patient population.

12. The method according to claim 11, further comprising the step of:
generating gap data by comparing a standard care with a delivered care provided to said selected patients.

13. The method according to claim 12, further comprising the step of:
generating one or more reports that presents said gap data in a human readable format.

14. The method according to claim 10, further comprising the step of:
querying said information base to identify a subgroup of said patient population having a particular characteristic associated with at least one of said specific disease conditions.

15. The method according to claim 14, further comprising the step of:
updating said knowledge data in said knowledge base in response to a result of said query.

16. The method according to claim 10, further comprising the step of:
generating a web page containing a status of at least eight of said patients.

17. The method according to claim 16, wherein said status comprises a plurality of risk levels in each of a symptom category, a behavior category and a knowledge category.

18. The method according to claim 10, further comprising the step of:
integrating external data received from one or more sources external to both said first server and said second server into said information base.

19. A system comprising:
means for storing both (i) knowledge data in a knowledge base and (ii) information data in an information base, wherein an ontology specifies how said knowledge data applies to one or more specific disease conditions and a patient population; and
means for communicating with one or more selected devices of a plurality of patient devices via a network, including (i) a rendering engine configured to (a) generate one or more queries in response to both said knowledge data and said information data and (b) transmit said queries to said selected devices and (ii) a feedback engine configured to (a) receive one or more responses from said selected devices, (b) generate feedback data by processing said responses and (c) to update said information base with said feedback data, wherein said knowledge base comprises (i) a plurality of multi-dimensional models corresponding to a plurality of diseases and (ii) a plurality of location pointers that define a plurality of locations of a plurality of aspects of said diseases in said multi-dimensional models.

* * * * *